US012280039B2

(12) United States Patent
Opgenorth et al.

(10) Patent No.: US 12,280,039 B2
(45) Date of Patent: Apr. 22, 2025

(54) CANCER VACCINE COMPOSITIONS AND METHODS OF USE THEREOF

(71) Applicant: Colorado State University Research Foundation, Fort Collins, CO (US)

(72) Inventors: Terry Opgenorth, Fort Collins, CO (US); Amanda Guth, Fort Collins, CO (US); Raymond Goodrich, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 1133 days.

(21) Appl. No.: 16/982,887

(22) PCT Filed: Mar. 21, 2019

(86) PCT No.: PCT/US2019/023320
§ 371 (c)(1),
(2) Date: Sep. 21, 2020

(87) PCT Pub. No.: WO2019/183320
PCT Pub. Date: Sep. 26, 2019

(65) Prior Publication Data
US 2021/0000936 A1  Jan. 7, 2021

Related U.S. Application Data

(60) Provisional application No. 62/755,741, filed on Nov. 5, 2018, provisional application No. 62/688,051, filed on Jun. 21, 2018, provisional application No. 62/645,975, filed on Mar. 21, 2018.

(51) Int. Cl.
*A61P 35/00* (2006.01)
*A61K 31/138* (2006.01)
*A61K 31/4178* (2006.01)
*A61K 31/525* (2006.01)
*A61K 39/00* (2006.01)
*A61K 39/39* (2006.01)
*A61K 47/26* (2006.01)
*A61N 5/06* (2006.01)

(52) U.S. Cl.
CPC ........ *A61K 31/4178* (2013.01); *A61K 31/138* (2013.01); *A61K 31/525* (2013.01); *A61K 39/0011* (2013.01); *A61K 39/39* (2013.01); *A61K 47/26* (2013.01); *A61N 5/06* (2013.01); *A61P 35/00* (2018.01); *A61K 2039/5152* (2013.01); *A61N 2005/0661* (2013.01)

(58) Field of Classification Search
CPC .............. A61K 39/0011; A61K 31/138; A61K 31/4178; A61K 31/525; A61K 39/39; A61K 47/26; A61K 2039/5152; A61N 5/06; A61N 2005/0661; A61P 35/00
See application file for complete search history.

(56) References Cited

U.S. PATENT DOCUMENTS

| 3,932,657 | A | 1/1976 | Rahman |
| 4,235,871 | A | 11/1980 | Papahadjopoulos et al. |
| 4,311,712 | A | 1/1982 | Evans et al. |
| 5,013,556 | A | 5/1991 | Woodle et al. |
| 5,395,619 | A | 3/1995 | Zalipsky et al. |
| 6,258,577 | B1 | 7/2001 | Goodrich, Jr. et al. |
| 6,277,337 | B1 | 8/2001 | Goodrich, Jr. et al. |
| 7,186,543 | B1 | 3/2007 | Goodrich |
| 8,759,092 | B2 | 6/2014 | Goodrich |
| 2002/0090358 | A1* | 7/2002 | Spaner ............... A61K 41/0023 435/372 |
| 2005/0063995 | A1* | 3/2005 | Spaner .................. A61K 41/17 424/277.1 |
| 2007/0212379 | A1 | 9/2007 | Goodrich |
| 2010/0112011 | A1 | 5/2010 | Friedberg |

FOREIGN PATENT DOCUMENTS

| CN | 107308515 A | 11/2017 |
| DE | 203 10 413 U1 | 1/2004 |
| WO | WO 03/035104 A2 | 5/2003 |
| WO | WO-2007044515 A1 | 4/2007 |
| WO | WO 2016/161309 A1 | 10/2016 |
| WO | WO-2019183320 A1 | 9/2019 |

OTHER PUBLICATIONS

Busam KJ et al. Expression of melan-A (MART1) in benign melanocytic nevi and primary cutaneous malignant melanoma (Am J Surg Pathol 1998 22(8):976-82) (Year: 1998).*
Speiser DE et al. Rapid and strong human CD8+ T cell responses to vaccination with peptide, IFA, and CpG oligodeoxynucleotide 7909. (J Clin Invest. 2005 115(3): 739-746) (Year: 2005).*
Chiang CL et al. Whole Tumor Antigen Vaccines: Where Are We? (Vaccines (Basel). 2015 3(2): 344-372.) (Year: 2015).*
Adams S et al. Toll-Like Receptor Agonists in Cancer Therapy. Immunotherapy. 2009 1(6): 949-964.) (Year: 2009).*
Zanettu-Polzi et al. Theoretical modeling of the absorption spectrum of aqueous riboflavin. (Chemical Physics Letters 669 (2017) 119-124) (Year: 2017).*
Goodrich et al., "Design and development of a method for the reduction of infectious pathogen load and inactivation of white blood cells in whole blood products," Biologicals, vol. 38, 2009, pp. 20-30.
Martin et al., "An Action Spectrum of the Riboflavin-photosensitized Inactivation of Lambda Phage," Photochemistry and Photobiology, vol. 81, 2005, pp. 474-480.

(Continued)

*Primary Examiner* — Karen A. Canella
*Assistant Examiner* — John J Skoko, III
(74) *Attorney, Agent, or Firm* — COOLEY LLP

(57) ABSTRACT

The disclosure provides a cancer vaccine composition comprising inactivated cancer cells and an adjuvant, wherein the inactivated cancer cells are incapable of replication. Also provided is a method for producing a cancer vaccine composition, the method comprising contacting cancer cells with light (e.g., UV light) in the presence of a photosensitizer (e.g., riboflavin).

19 Claims, 31 Drawing Sheets

(56) References Cited

OTHER PUBLICATIONS

Nicolaou K.C., et al., "Calicheamicin θ: A Rationally Designed Molecule with Extremely Potent and Selective DNA Cleaving Properties and Apoptosis Inducing Activity," Agnew, Chemie International Edition in English, 1994, vol. 33, pp. 183-186.
Park et al., "A Novel Cancer Immunotherapy Utilizing Autologous Tumor Tissue," Vox Sang., Aug. 2020, 115(6): 525-535.
Yin et al., "Effects of riboflavin and ultraviolet light treatment on pathogen reduction and platelets," Transfusion, vol. 60, Issue 11, 2020, pp. 2647-2654.
International Search Report and Written Opinion of the International Searching Authority for International Application No. PCT/US2019/023320 mailed Jul. 2, 2019, 14 pages.
Stevenson et al., "Photosensitization of guanine-specific DNA damage by 2-penylbenzimidazole and the sunscreen agent 2-phenylbenzimidazole-5-sulfonic acid," Chem. Res. Toxicol. 1989, 12, 38-45.
International Preliminary Report on Patentability dated Sep. 22, 2020 for PCT/US2019/023320, 9 pages.
Thakuri, et al., "Antibacterial photodynamic therapy on *Staphylococcus aureus* and pseudomonas aeruginosa in-vitro," Nepal Med Coll J 2011; 13(4):281-284.

\* cited by examiner

FIG. 16A-C

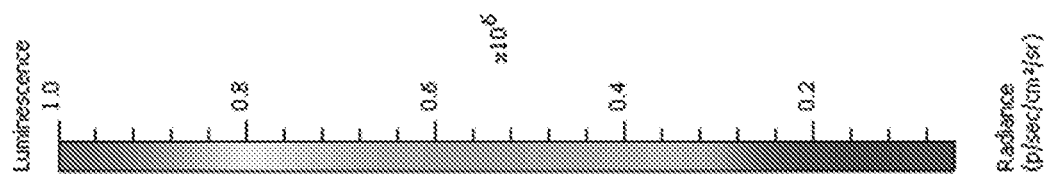
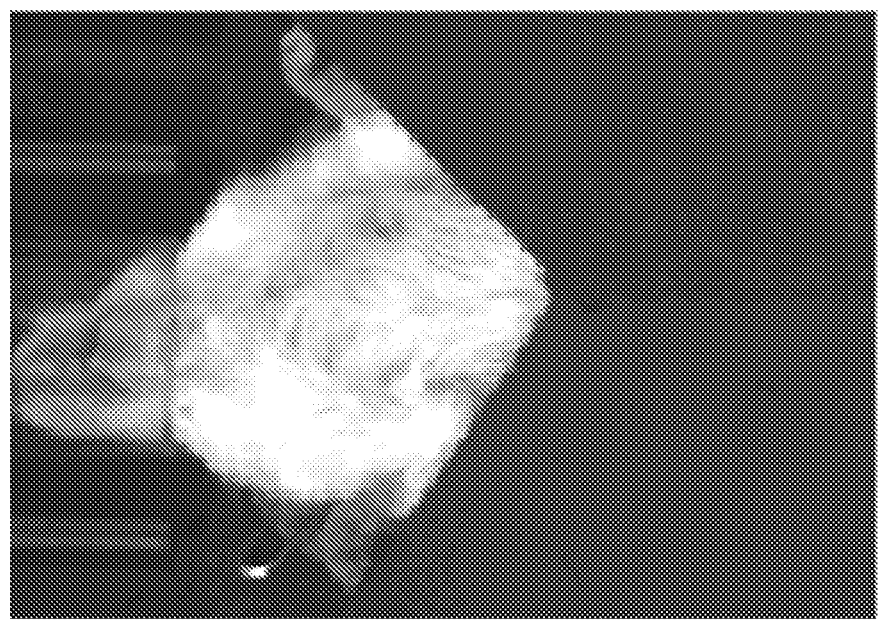
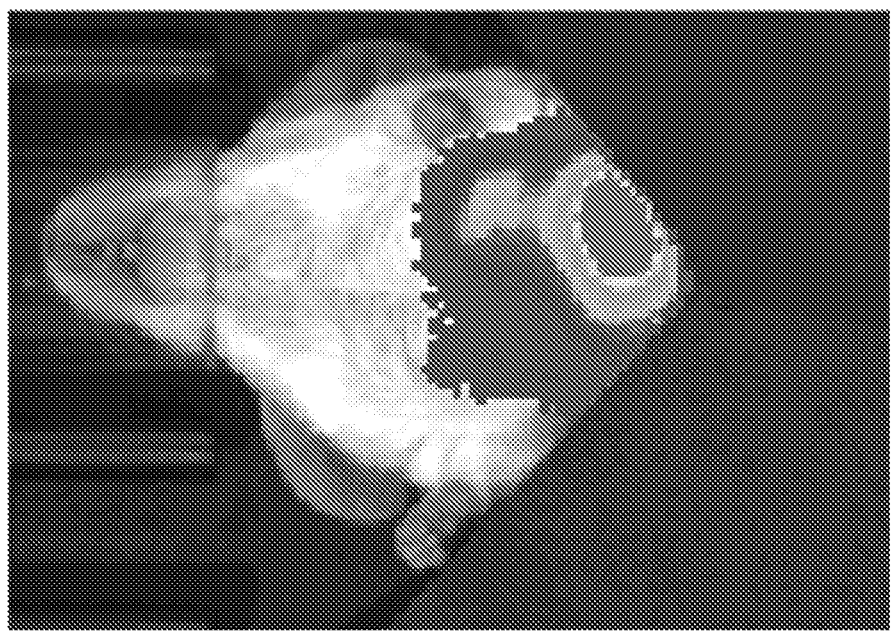
FIG. 19

| GLUT 1 | | |
|---|---|---|
| Antibody | Live | Inactivated Whole Cell Vaccine |
| Positive | 6.96% | 9.76% |
| Negative | 0.01% | 0.34% |
| HLA | | |
| Antibody | Live | Inactivated Whole Cell Vaccine |
| Positive | 75.56% | 42.51% |
| Negative | 0.07% | 0.10% |

CANCER VACCINE COMPOSITIONS AND METHODS OF USE THEREOF

CROSS REFERENCE TO RELATED APPLICATION

This application claims priority to U.S. Provisional Application Ser. No. 62/755,741, filed Nov. 5, 2018; U.S. Provisional Application Ser. No. 62/688,051, filed Jun. 21, 2018; and U.S. Provisional Application Ser. No. 62/645,975, filed Mar. 21, 2018, each of which is incorporated by reference herein in its entirety for all purposes.

TECHNICAL FIELD

The disclosure is generally related to compositions and methods for inhibiting tumor growth and promoting anti-tumor immune responses. More specifically, the disclosure is related to cancer vaccine compositions and methods that activate the immune system's response against a tumor. The disclosure also relates to methods for producing cancer cell vaccines.

BACKGROUND

Cancer immunotherapy involves the use of compositions and methods to elicit and enhance an individual's own immune system against cancerous cells, or infections that predispose to cancer. Cancer vaccines function by triggering the immune system to mount a response to an antigen (e.g., typically a protein, peptide, or carbohydrate) that is introduced into the body in a non-carcinogenic form and triggers the body to confer immunity or obtain a long-lived "memory" immune response. Once the immune system response is established, exposure of the immune system to this antigen (e.g., in the form of a cancerous tumor) results in a rapid and robust immune response.

One challenge for cancer immunotherapy is that clinical responses often vary considerably from one patient to another. Some patients can have remarkable and durable responses while other patients derive no apparent clinical benefit. Thus, there exists a need in the art for compositions that can reliably and effectively stimulate the immune system as a cancer immunotherapeutic.

SUMMARY

Provided herein is a cancer vaccine composition, the composition comprising inactivated cancer cells, wherein the inactivated cancer cells are incapable of replication. The cancer cells may be isolated or derived from a patient suffering from one or more types of cancer.

Also provided is a method for treating cancer in a patient in need thereof, the method comprising administering a cancer vaccine of the disclosure to the patient.

Also provided is a method for producing a cancer vaccine composition, the method comprising treating cancer cells with light (e.g., UV light) in the presence of a photosensitizer (e.g., riboflavin).

Also provided is a cancer vaccine composition for use in a method of treating cancer.

Also provided is a cancer vaccine composition for use as a medicament for treating cancer, and use of the cancer vaccine composition in the manufacture of a medicament for treating cancer. These and other aspects are described in further detail below.

BRIEF DESCRIPTION OF THE DRAWINGS

As shown in FIG. 11A, there was a significant decrease in measured metastatic burden in mice treated with the vaccine compared to adjuvant treated mice (Day 14, $p=0.0157$) and compared to both the control mice and adjuvant treated mice (Day 16, $p=0.0119$ and $p=0.0021$, respectively). FIG. 11B shows the photon flux data over time for the individual mice in each group.

FIG. 16A shows percent of T cells that were either CD4+CD25+(presumed T regulatory T cells) or CD8+ CD25+. There was a significant decrease in the CD4+ CD25+ T cells in the vaccinated mice. FIG. 16B shows percent CD8+ T cells expressing the immune suppressive proteins PD-1, Lag3 or Tim3.

FIG. 16C shows percent CD4+ T cells expressing the immune suppressive proteins PD-1, Lag3 or Tim3. For each data set shown in FIG. 16A-C, control is shown on the left and vaccine is shown on the right.

FIG. 19 shows the results of an experiment wherein metastatic disease in the lungs was quantitated using IVIS imaging after mice were injected with 4T1 mammary tumor cells that were then surgically removed and used to generate the inactivated whole cell vaccine. The mouse shown in the right panel was treated with an inactivated whole cell vaccine, and the mouse shown in the left panel was not given any vaccine. A scale bar for luminescence is also provided. 62% of mice receiving the vaccination were negative for lung metastases at similar time points wherein 80% of untreated mice had developed lung tumors at day 16 post-tumor cell removal.

DETAILED DESCRIPTION

Figure 1:
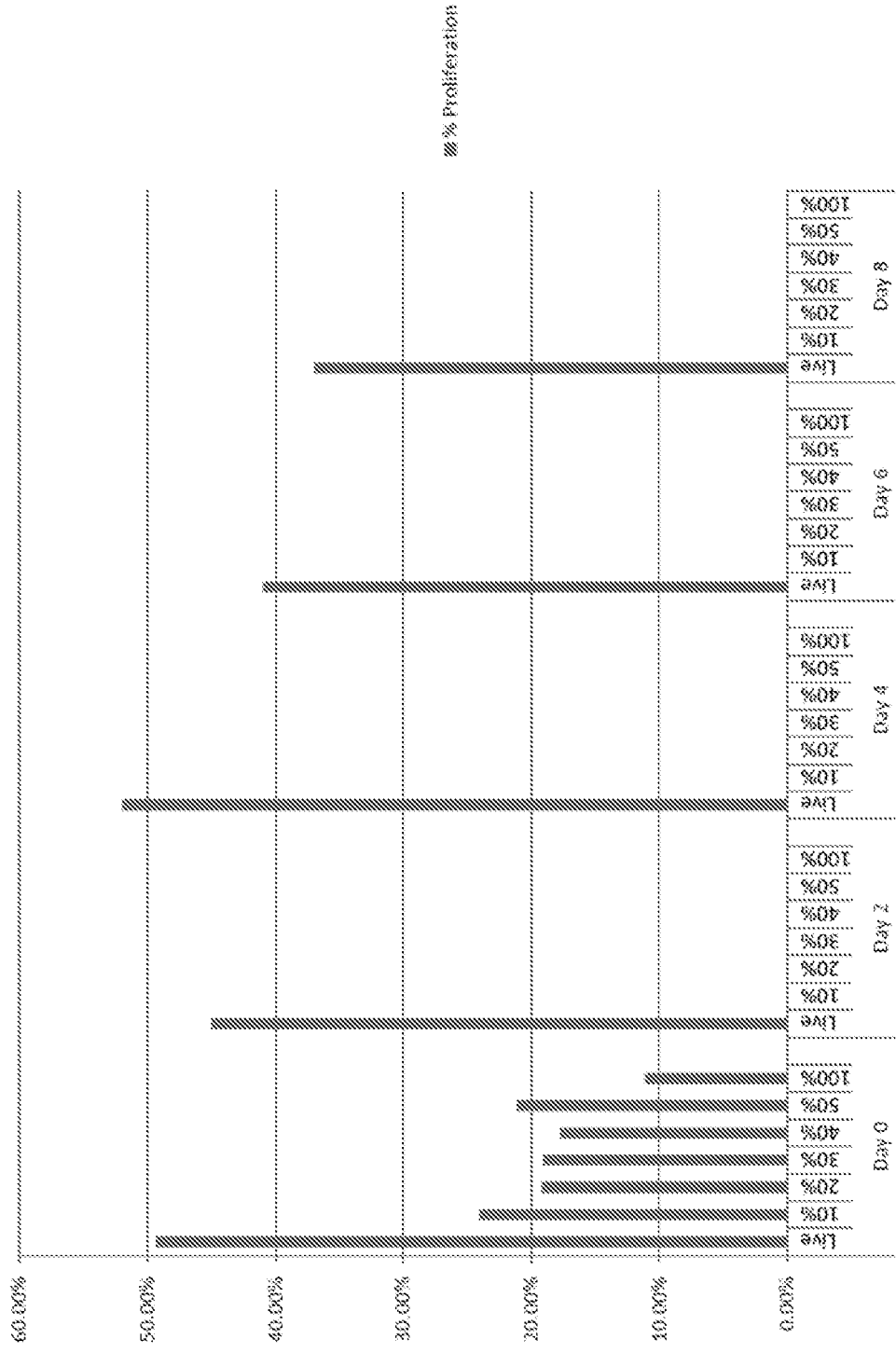
FIG. 1 illustrates proliferation of CAMA cells following treatment with riboflavin and UV light on the day of treatment (Day 0), and 2, 4, 6, and 8 days after treatment. Cells were treated using the Mirasol® PRT Illumination device, at 10%, 20%, 30%, 40%, 50% or 100% illumination intensities. Cells that were not treated with UV light (Live) were included as a control.

Provided herein is a method for inactivating cells and preventing their replication using UV light and riboflavin. This chemical process is specific to the DNA/RNA present in the cells. Thus, cellular DNA and/or RNA is modified, while leaving protein (including cell surface antigens, enzymes, etc.) untouched in the process. By preventing replication processes while preserving cell antigens and phenotype, the treated cancer cell preparations can be used as vaccine compositions. The fact that the antigens are present in their native state on the cells of the vaccine compositions may boost immune responses above the level observed with single antigens or protein formulations that are intended to elicit the same responses. The combination of inactivated whole cells with an adjuvant further boosts this immunological effect.

This technology can be used in an autologous or allogenic fashion, i.e. using tumor cells isolated from the patient, cancer stem cell preparations, or those grown in culture systems, etc. When administered to a patient, the whole cell vaccine reduces tumor growth, decreases metastasis, and prolongs survival time.

Thus, the technology described herein provides a rapid method to isolate, prepare and administer cancer cell vaccines to patients, producing a response in the patient that rivals use of standard chemotherapy drugs.

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

Definitions

The following terms are used in the description herein and the appended claims:

The singular forms "a," "an" and "the" are intended to include the plural forms as well, unless the context clearly indicates otherwise.

Furthermore, the term "about" as used herein when referring to a measurable value such as an amount, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features described herein can be used in any combination.

As used herein, the terms "reduce," "reduces," "reduction" and similar terms mean a decrease of at least about 10%, about 15%, about 20%, about 25%, about 35%, about 50%, about 75%, about 80%, about 85%, about 90%, about 95%, about 97% or more.

As used herein, the terms "enhance," "enhances," "enhancement" and similar terms indicate an increase of at least about 10%, about 15%, about 20%, about 25%, about 50%, about 75%, about 100%, about 150%, about 200%, about 300%, about 400%, about 500% or more.

By the terms "treat," "treating" or "treatment of" (and grammatical variations thereof) it is meant that the severity of the patient's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a patient and/or a reduction in the severity of the onset of the disease, disorder and/or clinical symptom(s) relative to what would occur in the absence of the methods of the disclosure. The prevention can be complete, e.g., the total absence of the disease, disorder and/or clinical symptom(s). The prevention can also be partial, such that the occurrence of the disease, disorder and/or clinical symptom(s) in the patient and/or the severity of onset is less than what would occur in the absence of the present disclosure.

"Therapeutically effective amount" as used herein refers to an amount that, when administered to a patient for treating a disease, or at least one of the clinical symptoms of a disease, is sufficient to affect such treatment of the disease or symptom thereof. The "therapeutically effective amount" may vary depending, for example, on the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

Cancer Vaccine Compositions

Provided herein are cancer vaccine compositions. The compositions comprise, consist essentially of, or consist of inactivated cancer cells, optionally in combination with an adjuvant. The cancer cells are inactivated by modifying their DNA and/or RNA, rendering them replication incompetent. The modification of the cellular DNA and/or RNA does not kill the cells, i.e. the cancer vaccines are live, replication-inactivated vaccines. Because cell viability is maintained, the vaccines present live antigenic targets to the patient's immune system. Peripheral inoculation stimulates immune response to primary tumor and metastases.

In some embodiments, the cancer vaccine comprises, consists essentially of, or consists of cancer cells that were inactivated using a photochemical process to inactivate tumor cell DNA and/or RNA replication while preserving protein structure and phenotype. In some embodiments, the DNA and/or RNA of the cancer cells in the cancer cell vaccine comprises modified bases. For example, in some embodiments, the DNA of the cancer cells in the vaccine may comprise modified guanine bases, such as oxidized guanine bases.

In some embodiments, the cancer cells are autologous cancer cells. As used herein "autologous" refers to cells that were removed from or derived from the same patient to whom the vaccine is administered. In some embodiments, the cancer cells are allogeneic cells. As used herein, "allogeneic" refers to cells that were removed from or derived from a donor who is not the patient to whom the vaccine is administered.

In some embodiments, the cancer cells are from a patient suffering from one or more types of cancer. For example, the cancer cells may be isolated or derived from a patient suffering from cancer. The cancer may be a solid tumor or a liquid tumor. The cancer cells may be isolated or derived from a primary tumor, or a metastatic tumor. The cancer may be stage I, stage II, stage III, or stage IV. In some embodiments, the cancer cells may be derived from a patient suffering from breast cancer, lung cancer, liver cancer, bladder cancer, gynecological cancer, brain cancer, stomach cancer, prostate cancer, skin cancer, thyroid cancer, pancreatic cancer, colon cancer, or blood cancer. In some embodiments, the skin cancer is a melanoma. In some embodiments, the blood cancer is a leukemia, a lymphoma, or a myeloma. In some embodiments, the leukemia is Acute Lymphocytic Leukemia or Acute Myeloid Leukemia. In some embodiments, the lymphoma is Hodgkin's Lymphoma or Non-Hodgkins Lymphoma. In some embodiments, the myeloma is multiple myeloma.

In some embodiments, the cancer cells are derived from an immortalized cancer cell line. As used herein, a "cancer cell line" refers to a transformed cell line derived from a cancer sample. Usually, a cancer cell line is capable of generating a tumor upon explant into an appropriate host. A cancer cell line usually retains, in vitro, properties in common with the cancer from which it is derived, including, e.g., loss of differentiation, loss of contact inhibition, and will undergo essentially unlimited cell divisions in vitro. Cancer cell lines may include cell lines which have been genetically modified, for example, to express a protein that allows the cells to be recognized better by antigen-presenting cells.

In some embodiments, the cancer cells are cancer stem cells.

In some embodiments, the cells are derived from a non-cancerous but abnormal growth, i.e., a benign tumor or growth.

In some embodiments, the cancer vaccine comprises, consists essentially of, or consists of white blood cells (e.g., tumor-associated macrophages), tumor-associated endothelial cells, tumor-associated fibroblasts, or any other cell type present in the tumor m icro-environment.

In some embodiments, the cancer vaccine composition further comprises an adjuvant. The effect of the adjuvant is to boost the immunological response. In some embodiments, the adjuvant modifies monocyte function.

Examples of suitable adjuvants include saponin formulations, virosomes, virus like particles, non-toxic derivatives of enterobacterial lipopolysaccharide (LPS), immunostimulatory oligonucleotides (e.g. an immunostimulatory oligonucleotide containing a CpG motif), mineral containing compositions, oil-emulsions, polymers, micelle-forming adjuvants (e.g., a liposome), immunostimulating complex matrices (e.g., ISCOMATRIX), particles, squalene, phosphate, cationic liposome-DNA complexes (CLDC), DDA, DNA adjuvants, gamma-insulin, ADP-ribosylating toxins, detoxified derivatives of ADP-ribosylating toxins, Freund's complete adjuvant, Freund's incomplete adjuvant, muramyl dipeptides, monophosphoryl Lipid A (MPL), poly IC, CpG oligodeoxynucleotides (ODNs), imiquimod, adjuvant system AS01, adjuvant system AS02, adjuvant system AS03, MF59® and aluminum or aluminum salts (e.g. alum, aluminum phosphate, aluminum hydroxide). Other suitable adjuvants include TLR agonists, NOD agonists, and lipid-DNA agonist complexes.

In some embodiments, the cancer vaccine composition further comprises one or more agonists or antagonists.

In some embodiments, the agonist comprises a Toll-Like Receptor (TLR) agonist. In some embodiments, the TLR agonist is an agonist of TLR1, TLR2, TLR3, TLR4, TLR5, TLR6, TLR7, TLR8, TLR9, TLR10, TLR11, or TLR12. In particular embodiments, the agonist is a TLR3 and/or a TLR9 agonist.

In some embodiments, the antagonist is a C—C chemokine receptor type 2 (CCR2) antagonist.

In some embodiments, the antagonist is an angiotensin receptor blocker (ARB), such as losartan, telmisartan, irbesartan, azilsartan, candesartan, eprosartan, olmesartan, or valsartan. In some embodiments, the ARB is administered at a dose of between about 5 and about 100 mg/kg, for example about 5, about 10, about 15, about 20, about 25, about 30, about 35, about 40, about 45, about 50, about 55, about 60, about 65, about 70, about 75, about 80, about 85, about 90, about 95, or about 100 mg/kg.

In some embodiments, the cancer vaccine comprises at least one of (i.e. one of, two of, or all three of) a TLR agonist, a CCR2 antagonist and an ARB.

In some embodiments, the agonist or antagonist (e.g., TLR3 and/or a TLR9 agonist) is contained within or coupled to a liposome. Liposomes are spherical, self-enclosed vesicles composed of amphipathic lipids. Liposomes may be unilamellar, having one lipid bilayer membrane, or multilamellar, having two or more concentrically arranged bilayers. Suitable liposomes may have a selected mean particle size diameter of about 200-500 nm. Various methods of preparing liposomes and encapsulation of therapeutic agents therein are well documented (see, for example, U.S. Pat. Nos. 3,932,657, 4,311,712, and 5,013,556, all of which are incorporated herein by reference). Known methods include the reverse phase evaporation method as described in U.S. Pat. No. 4,235,871, which is incorporated herein by reference.

Lipids for use in forming the liposomes described herein include vesicle-forming lipids having two hydrocarbon chains, typically acyl chains, and a polar head group. Included in this class are the phospholipids, such as phosphatidylcholine (PC), phosphatidylethanolamine (PE), phosphatidic acid (PA), phosphatidylinositol (PI), and sphingomyelin (SM), where the two hydrocarbon chains are typically between about 14-22 carbon atoms in length, and have varying degrees of unsaturation. The selection of lipids and proportions can be varied to achieve a desired degree of fluidity or rigidity, to control stability, and/or to control the rate of release of an entrapped agent. Where more than one type of lipid is used, a suitable amount of a relatively unsaturated lipid (such as PC), may be used in order to form stable liposomes. In one embodiment, at least 45-50 mol % of the lipids used to form the liposome are PC.

The liposomes may also include lipids derivatized with a hydrophilic polymer such as polyethylene glycol (PEG). Suitable hydrophilic polymers include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide, and hydrophilic peptide sequences. Methods of preparing lipids derivatized with hydrophilic polymers are known (see e.g. U.S. Pat. No. 5,395,619, which is incorporated herein by reference).

In some embodiments, the cancer vaccine comprises cationic liposome-DNA complexes (CLDC).

In some embodiments, the cancer vaccine further comprises a photosensitizer such as riboflavin (vitamin B2). In some embodiments, the cancer vaccine is substantially free of photosensitizer.

In some embodiments, the cancer vaccine composition further comprises a carrier. In some embodiments, the cells and/or the photosensitizer are suspended in the carrier. In some embodiments, the carrier comprises normal saline (e.g., 0.9% sodium chloride), dextrose saline (e.g., dextrose 5% in 0.9% sodium chloride), phosphate buffered saline (e.g., 137 mmol/L NaCl, 2.7 mmol/L KCl, 10 mmol/L $Na_2HPO_4$, 2 mmol/L $KH_2PO_4$).

In some embodiments, the cancer vaccine composition further comprises one or more additional pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilizers, solubilizers, surfactants (e.g., wetting agents), masking agents, coloring agents, flavoring agents, and sweetening agents. Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, New York, USA), *Remington's Pharmaceutical Sciences,* 20th edition, pub. Lippincott, Williams & Wilkins, 2000; and *Handbook of Pharmaceutical Excipients,* 2nd edition, 1994.

Methods of Producing Cancer Cell Vaccines

Figure 20:
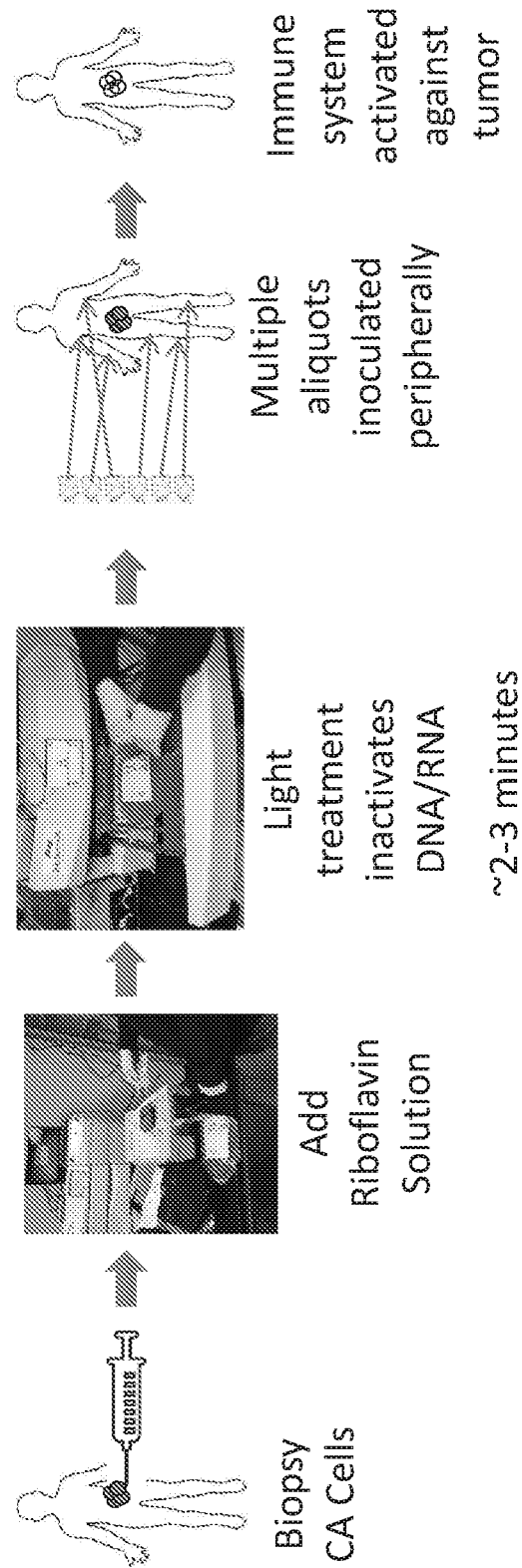
FIG. 20 depicts an exemplary scheme for inactivating cells using UV light and riboflavin, preparing a vaccine composition, and treating a patient in need thereof.

The cancer cell vaccines described herein are produced using an innocuous chemical agent in a selective process that prevents cellular replication processes while preserving antigenic protein structure. More specifically, the cancer cell vaccines are produced by the combined application of a photosensitizer and light for rendering cancer cells replication deficient while retaining other biological functions of the treated cells and proteins. An exemplary scheme for producing and using cancer cell vaccines is shown in FIG. 20. The process for producing the cancer vaccines of the disclosure is described in detail below.

Initially, cancer cells are provided. The cancer cells may be autologous, i.e. removed from or derived from the subject to be vaccinated. In some embodiments, the cancer cells may be allogeneic. The cancer cells may also be derived from a cancer cell line.

In some embodiments, the cancer cells are cancer stem cells. In some embodiments, the cancer vaccine comprises, consists essentially of, or consists of white blood cells (e.g., tumor-associated macrophages), tumor-associated endothelial cells, tumor-associated fibroblasts, or any other cell type present in the tumor micro-environment.

In some embodiments, the cancer cells are provided as a single cell suspension during inactivation. In some embodiments, the cells are suspended in media during inactivation. Exemplary medias which may be used include, but are not limited to, RPMI1640, MEM, DMEM, IMDM, DMEM-F12, Opti-MEM, Ham's F12, Media 199, or combinations thereof.

Next, the cancer cells are inactivated using photochemical technology. This is achieved using photosensitizers that can act as electron transfer agents. The application of photosensitizer agents that can be placed into an excited state in proximity to a guanine base in DNA or RNA constructs allows for selective modification (e.g. oxidation, cross-linking, fragmentation, deamination) of these bases. Because electron chemistry can only occur over short distances, the photosensitizer agent must be bound or associated with (i.e. intercalated with) the nucleic acid in order to carry out the desired chemistry.

In some embodiments, the photosensitizer is a flavin, for example riboflavin (Vitamin B2), flavin mononucleotide, or flavin adenine dinucleotide. In some embodiments, the photosensitizer is a tertiary aliphatic amine (e.g., 1,4-diazabicyclo(2,2,2)octane), a piperazine, (e.g., N-2-hydroxyethylpiperazine-N'-2-ethanesulfonic acid and 1,4-dimethylpiperazine), an amino acid (e.g., tyrosine, tryptophan, histidine, methionine), an enzyme (e.g., superoxide dismutase) or EDTA (ethylenediaminetetraacetic acid). In some embodiments, the photosensitizer is riboflavin.

The cells are added to a solution containing the photosensitizer (e.g. riboflavin), or the photosensitizer is added to a solution containing the cells (e.g., a single cell suspension of the cells in media).

In some embodiments, the concentration of photosensitizer used during inactivation is about 10 µM to about 100 µM, such as about 10 µM, about 15 µM, about 20 µM, about 25 µM, about 30 µM, about 35 µM, about 40 µM, about 45 µM, about 50 µM, about 55 µM, about 60 µM, about 65 µM, about 70 µM, about 75 µM, about 80 µM, about 85 µM, about 90 µM, about 95 µM, or about 100 µM. In some embodiments, the solution contains the photosensitizer at a concentration of about 1 µM to about 50 µM, such as about 2 µM, about 3 µM, about 4 µM, about 5 µM, about 6 µM, about 7 µM, about 8 µM, about 9 µM, about 10 µM, about 15 µM, about 20 µM, about 25 µM, about 30 µM, about 35 µM, about 40 µM, about 45 µM, or about 50 µM. In some embodiments, the photosensitizer concentration is less than about 10 µM, such as less than about 9 µM, about 8 µM, about 7 µM, about 6 µM, about 5 µM, about 4 µM, about 3 µM, about 2 µM, or about 1 µM.

The solution containing the photosensitizer and the cells (optionally, in media) is then subjected to light treatment. The light treatment may comprise treatment with visible light, ultraviolet light, and/or infrared light. The light treatment inactivates DNA and/or RNA in the cancer cells by modifying bases of these nucleic acids. In some embodiments, guanine bases are selectively modified. In some embodiments, guanine bases are selectively oxidized. Oxidized guanine bases cannot be repaired by natural enzymatic and cell repair mechanisms. As such, there is no possibility for reversion of the induced change to a form that would restore the ability of the cells to replicate.

In some embodiments, the light treatment comprises, consists essentially of, or consists of treatment with ultraviolet (UV) light. The UV light may be UV-A, UV-B, or UV-C light. The UV light may have a wavelength of 170 to 400 nm, including all ranges and subranges therebetween. For example, in some embodiments, the UV light has a wavelength of 315 to 400 nm, 310 to 320 nm, 280 to 360 nm, 280 to 315 nm, or 180 to 280 nm. The UV light may be provided by UV light sources known in the art, such as the Mirasol® PRT Illumination device (TerumoBCT, Lakewood, Colorado). In some embodiments, the cells may be treated with multiple wavelengths of light simultaneously.

In particular embodiments, when riboflavin is used as a photosensitizer, UV light having a wavelength of 310 to 320 nm is used. The inventors have determined that this wavelength prevents riboflavin from reacting in free solution, which results in production of undesirable oxygen free radicals. At these wavelengths, riboflavin will selectively react when intercalated with nucleic acid.

The dose of the UV light may vary depending on the volume of solution being treated. For example, the dose of the UV light may be between 200-400 Joules (e.g., 300 Joules) for a volume of about 170 to 370 mls of solution. As will be understood by those of skill in the art, the dosage may be adjusted up or down if the volume to be treated is above or below this range.

In some embodiments, the dose of UV light may be from about 200 Joules to about 600 Joules, for example about 200, about 225, about 250, about 275, about 300, about 325, about 350, about 375, about 400, about 425, about 450, about 475, about 500, about 525, about 550, about 575, or about 600 Joules. In some embodiments, the volume of cancer cell preparations for illumination may be from about 200 ml to about 600 ml, for example about 200, about 225, about 250, about 275, about 300, about 325, about 350, about 375, about 400, about 425, about 450, about 475, about 500, about 525, about 550, about 575, or about 600 ml. In some embodiments, the dose of UV light may be from about 0.5 J/ml to about 3.0 J/m l. For example, the dose of UV light may be about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 Joules/ml.

The cells may be treated with UV light for about 1 minute to about 60 minutes, for example, about 1, about 2, about 3, about 4, about 5, about 6, about 7, about 8, about 9, about 10, about 15, about 20, about 25, about 30, about 35, about 40, about 45, about 50, about 55, or about 60 minutes. In some embodiments, the cells are treated with UV light for about 1 minute to about 10 minutes, about 1 minute to about 5 minutes, or about 1 minute to about 3 minutes.

In some embodiments, the cancer cells are preincubated for a predetermined period of time in the solution containing the photosensitizer (e.g., riboflavin) before subjecting the cells to the light treatment.

In some embodiments, the cells are not subjected to any additional purification or modification steps after light treatment. In other embodiments, the cancer cells are isolated and/or washed after the light treatment. For example, the cells may be pelleted and optionally washed after the light treatment. Pelleting and/or washing the cells may substantially remove photosensitizer (e.g., riboflavin) from the composition. In some embodiments, the cancer cells are concentrated after the light treatment.

In some embodiments, the cancer cells are resuspended or combined with one or more additional pharmaceutically acceptable ingredients as described above after light treatment. In some embodiments, the cancer cells are resuspended in a solution comprising an adjuvant after light treatment.

In some embodiments, the cells remain viable for 1, 2, 3, 4, 5, 6, 7, 8, 9 or 10 days after light treatment. In some embodiments, the cells die (e.g., by an apoptotic mechanism) 1, 2, 3, 4, 5, 6, 7, 8, 9, or 10 days after treatment.

The cells generated using this method are incapable of replication processes, but substantially maintain and preserve the antigen and epitope profile of the original, native cell or antigen under treatment. In some embodiments, the inactivation process does not substantially change the metabolic processes, phenotype, or structure of the cancer cells. For example, in some embodiments, the inactivation process does not substantially change cell-surface marker expression in the cancer cells. In some embodiments, the inactivation process does not substantially change expression levels of cell surface markers such as EpCAM, CD38, CD34, CD117, CD44, CD24, Sca1, HLA, Glut1, MHC Class I, PDL-L1, CD45, gp70, GFP and/or CD90 in the cells. In some embodiments, the inactivation process does not compromise the cell membrane and nuclear membrane integrity of the cells.

The fact that the cells are replication incompetent protects against native forms of the disease (cancer) or altered cell compositions in the body responsible for formation of tumorous lesions. Thus, because the specificity of the chemistry preserves the antigen profile and cellular integrity, and maintains protein structure in its native state, the inactivated cells that are produced by this process provide an improved source for antigen presentation.

Methods of Treatment

The cancer cell vaccine compositions described herein can be used as vaccine agents or stimulants for immune system priming and recognition that foster immune responses in cancer patients. This targeted therapy results in fewer side effects compared to traditional treatments such as chemotherapy or radiation. Notably, because the cancer cells of the vaccine maintain a normal phenotype, the potential for them to induce undesired side effects is extremely low or nonexistent.

In some embodiments, the cancer cell vaccine may be administered to a patient to treat or prevent cancer in the patient. The cancer that is treated or prevented may be a solid tumor or a liquid tumor. For example, the cancer that is treated or prevented may be breast cancer, lung cancer, liver cancer, bladder cancer, gynecological cancer, brain cancer, stomach cancer, prostate cancer, skin cancer, thyroid cancer, pancreatic cancer, colon cancer, or blood cancer. In some embodiments, the skin cancer is a melanoma. In some embodiments, the blood cancer is a leukemia, a lymphoma, or a myeloma. In some embodiments, the leukemia is Acute Lymphocytic Leukemia or Acute Myeloid Leukemia. In some embodiments, the lymphoma is Hodgkin's Lymphoma or Non-Hodgkin's Lymphoma. In some embodiments, the myeloma is multiple myeloma.

In some embodiments, the vaccine may be administered to a patient to treat or prevent a non-cancerous but abnormal growth, i.e., a benign tumor or growth, in a patient. While most benign tumors/growths are treatable with surgery, some are in locations where surgery is not possible, and/or radiation may not be adequate. Examples of non-cancerous growths that may be treated include, but are not limited to, adenomas, fibromas, neuromas, hemangiomas, seborrheic keratoses, dermatosis papulosa nigra, and sebaceous hyperplasia.

In some embodiments, the patient is assessed for immune function and immune status prior to administration of the cancer vaccine. Such assessments may include, but are not limited to, DTH skin testing, blood tests, lymph node aspirate tests, tumor tissue tests, and/or determination of whether the patient is anergic, B cell responsive, etc. In some embodiments, the patient is not assessed for immune function and immune status prior to administration of the cancer vaccine.

In some embodiments, the patient may be immunocompetent. In other embodiments, the patient may be immunocompromised. Optionally, the vaccine may be used in combination with genetic testing to quantify the degree of immune-responders, or immune non-responders.

It will be appreciated by one of skill in the art that appropriate number of cells in the cancer vaccine composition can vary from patient to patient. In some embodiments, the cancer vaccine comprises about $1\times10^3$, about $1\times10^4$, about $1\times10^5$, about $1\times10^6$, about $1\times10^7$, about $1\times10^8$, about $1\times10^9$, or about $1\times10^{10}$ cells. In some embodiments, a cancer vaccine comprises about $1\times10^5$ to about $1\times10^8$ cells.

In some embodiments, about $1\times10^5$ to about $1\times10^8$ cells are administered to a patient per administration. For example, about $1\times10^5$, about $5\times10^5$, about $1\times10^6$, about $5\times10^6$, about $1\times10^7$, about $5\times10^7$, or about $1\times10^8$ cells may be administered to a patient per administration. In some embodiments, the administered dose is a split dose, wherein the total number of cells for administration is divided into 2, 3, 4, 5, 6, 7, 8, 9, or 10 sub-doses. One or more sub-dose may be administered to the patient peripherally, at different locations on the patient's body. Each sub-dose may be administered at approximately the same time, or administration of the sub-doses may be staggered. For example, sub-doses may be administered at intervals of 15 minutes, 20 minutes, 30 minutes, 45 minutes, 1 hour, or 3 hours.

In some embodiments, the cancer vaccine is administered once, or more than once to the patient. In some embodiments, the cancer vaccine is administered once, twice, three times, four times, five times, six times, seven times, eight times, nine times, or ten times to a patient.

The cancer vaccine may be administered to the patient every day, about every 3 days, about every 7 days, about every fourteen days, about once per month, or about once per year. In some embodiments, the cancer vaccine is administered at least once per week, at least every two weeks, or at least once every six months. In some embodiments, the cancer vaccine is administered once, twice, three times, four times, five times, six times, seven times, eight times, nine times, ten times, twelve times, fifteen times, twenty times, or twenty-five times in a year.

In some embodiments, a first cancer vaccine and a second cancer vaccine are administered to the patient. In some embodiments, the second cancer vaccine is administered after the first vaccine to boost the immune response. In some embodiments, immune response and/or tumor growth in the patient are monitored between administration of the first vaccine and the second vaccine. In some embodiments, the second cancer vaccine is administered when it is determined that the patient has not exhibited a satisfactory immune response following administration of the first vaccine, or when it is determined that the tumor has continued to grow or metastasize after administration of the first vaccine. In some embodiments, the first cancer vaccine and the second vaccine comprise cells isolated or derived from a first tumor extraction. For example, a tumor removed from a patient may be used to produce the first and second vaccine, and after the first vaccine is administered, the second vaccine is stored for later use. In some embodiments, the first vaccine and the second vaccine comprise cells isolated or derived from separate tumor extractions. For example, a tumor removed from a patient may be used to produce the first vaccine, and after the tumor recurs or metastasizes, the recurrent tumor or metastatic tumor is removed and used to produce the second vaccine.

The cancer vaccine may be delivered to the patient intramuscularly, intramucosally, intranasally, subcutaneously, intratumorally, intradermally, transdermally, intravaginally, intraperitoneally, intrarectally, intra-articularly or intra-lymphatically, orally or intravenously. In some embodiments, administration may be by sublingual, buccal, intra-organ (e.g., intrasplenic), or inhaled routes. For intravenous, cutaneous or subcutaneous injection, or injection at the site of the tumor, the cancer cell vaccine may be in the form of a parenterally acceptable aqueous solution which has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

In some embodiments, the vaccine is administered peripherally to the patient. In some embodiments, multiple aliquots of the cancer vaccine are administered peripherally to the patient, in different locations.

In some embodiments, the cancer vaccine is administered simultaneously or sequentially (either before or after) with a vaccine-enhancing agent. In some embodiments, the vaccine-enhancing agent is an angiotensin receptor blocker (ARB) or a beta blocker (BB). Exemplary vaccine-enhancing agents include losartan, telmisartan, irbesartan, azilsartan, candesartan, eprosartan, olmesartan, valsartan, propranolol, acebutolol, atenolol, betaxolol, bisoprolol, carteolol, carvedilol, esmolol, labetalol, metoprolol, nadolol, nebivolol, penbutolol, pindolol, propranolol, sotalol, timolol. In some embodiments, the vaccine-enhancing agent is selected from the group consisting of losartan and propranolol. In some embodiments, the vaccine-enhancing agent is losartan. In some embodiments, the vaccine-enhancing agent is propranolol.

In some embodiments, the vaccination protocol described herein comprises administering a cancer cell vaccine composition comprising inactivated, live cancer cells, and a potent adjuvant comprising TLR3 and/or TLR9 agonists attached to liposomes, and also comprises sequential or simultaneous administration of a vaccine-enhancing agent (e.g., losartan), which is given at or around the time of vaccination and reduces recruitment of immune suppressive myeloid cells.

In some embodiments, the vaccination protocol described herein comprises administering a cancer cell vaccine composition comprising inactivated, live cancer cells to a patient in need thereof. An adjuvant may optionally be administered at the time of vaccination. In some embodiments, an adjuvant is administered after vaccination to boost the immune response, for example about 6 hours, about 12 hours, about 24 hours, about 36 hours, about 48 hours, about 60 hours, or about 72 hours after vaccination. In some embodiments, the adjuvant comprises liposomes, e.g., CLDC. In some embodiments, a vaccine-enhancing agent such as losartan may be administered at or around the time of the vaccination. In some embodiments, a vaccine-enhancing agent such as losartan may be administered after vaccination, for example, about 6 hours, about 12 hours, about 24 hours, about 36 hours, about 48 hours, about 60 hours, or about 72 hours after vaccination. In some embodiments, a vaccine-enhancing agent such as losartan may be administered to the patient daily for a therapeutically effective number of days, optionally beginning on the day that the vaccine is administered. In some embodiments, the vaccine-enhancing agent (e.g., losartan) is administered at a dose of between about 5 and about 100 mg/kg, for example about 5, about 10, about 15, about 20, about 25, about 30, about 35, about 40, about 45, about 50, about 55, about 60, about 65, about 70, about 75, about 80, about 85, about 90, about 95, or about 100 mg/kg.

In some embodiments, the treatment reduces tumor growth or regrowth by at least 10%, at least 20%, at least 30%, at least 40%, at least 50%, at least 60%, at least 70%, at least 80%, at least 85%, at least 90%, at least 95%, or 100% compared to tumor growth in an unvaccinated patient. In some embodiments, the treatment prolongs survival of the patient by at least 10%, at least 20%, at least 30%, at least 40%, at least 50%, at least 60%, at least 70%, at least 80%, at least 85%, at least 90%, at least 95%, or 100% compared to an unvaccinated patient. In some embodiments, the treatment reduces the occurrence of metastasis by at least 10%, at least 20%, at least 30%, at least 40%, at least 50%, at least 60%, at least 70%, at least 80%, at least 85%, at least 90%, at least 95%, or 100% compared to an unvaccinated patient.

The cancer cell vaccine may elicit an immune response in the patient. In some embodiments, the immune response may include one or more of the following: (i) upregulation of immunoglobulin (e.g., IgG, IgM), (ii) T-cell activation (e.g., multiple T-cell generations matched to multiple cancer neoantigens), (iii) modulation of innate immune cells (e.g., myeloid cells), and (iv) revival of "exhausted" T-Cell populations.

Suitable patients include both avians and mammals. The term "avian" as used herein includes, but is not limited to, chickens, ducks, geese, quail, turkeys, pheasant, parrots, parakeets, and the like. The term "mammals" as used herein includes, but is not limited to, humans, non-human primates, bovines, ovines, caprines, equines, felines, canines, lagomorphs, etc. Human subjects include neonates, infants, juveniles, adults and geriatric subjects. The terms "subject" and "patient" are used interchangeably herein.

The cancer cell vaccines may be administered to patients with pre-existing conditions, for example pre-existing conditions that would prevent treatment with other therapies such as radiation, chemotherapy, or surgical resection.

Combination Therapies

The cancer cell vaccines may be administered alone or in combination with other treatments/therapies, either simultaneously or sequentially, depending upon the condition to be treated. Examples of treatments and therapies include, but are not limited to, chemotherapy (the administration of active agents, including, e.g. drugs, such as chemotherapeutics); surgery; and radiation therapy. Further examples of treatments and therapies include immune-based therapies, such as antibody therapy, adoptive cell therapy (ACT), and vaccine-based therapy. In some embodiments, the cancer cell vaccines described herein may be administered after another treatment/therapy to eliminate any remaining tumor cells.

In some embodiments, the cancer vaccines may be administered in combination with one or more of the following therapies: checkpoint inhibitors (e.g., PD-1 or PDL-1 inhibitors, antibody therapies, genetically engineered dendritic cells, or genetically engineered T-cells (e.g., CAR-T cells).

In some embodiments, the cancer vaccines may be administered alone or in combination with a chemotherapeutic agent. A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of suitable chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSARC)); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylene-thiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omegaII (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the vaccines of the disclosure include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Numbered Embodiments of the Invention

1. A cancer vaccine composition, the composition comprising inactivated cancer cells, wherein the inactivated cancer cells are incapable of replication.
2. The cancer vaccine composition of embodiment 1, wherein the cancer cells are from a patient suffering from one or more types of cancer.
3. The cancer vaccine composition of embodiment 2, wherein the patent is suffering from one or more of breast cancer, lung cancer, liver cancer, bladder cancer, gynecological cancer, brain cancer, stomach cancer, prostate cancer, skin cancer, thyroid cancer, pancreatic cancer, colon cancer, and blood cancer.
4. The cancer vaccine composition of embodiment 3, wherein the skin cancer is a melanoma.
5. The cancer vaccine composition of embodiment 3, wherein the blood cancer is a leukemia, a lymphoma, or a myeloma.
6. The cancer vaccine composition of embodiment 5, wherein the leukemia is Acute Lymphocytic Leukemia or Acute Myeloid Leukemia.
7. The cancer vaccine composition of embodiment 5, wherein the lymphoma is Hodgkin's Lymphoma or Non-Hodgkin's Lymphoma.
8. The cancer vaccine composition of embodiment 5, wherein the myeloma is multiple myeloma.
9. The cancer vaccine composition of embodiment 2, wherein the patent is suffering from a benign tumor.
10. The cancer vaccine composition of embodiment 2, wherein the cancer is metastatic cancer.
11. The cancer vaccine composition of any one of embodiments 1-10, wherein the cancer cells are derived from an immortalized cell line.
12. The cancer vaccine composition of any one of embodiments 1 to 11, wherein the cancer cells are autologous.
13. The cancer vaccine composition of any one of embodiments 1 to 11, wherein the cells are allogeneic.
14. The cancer vaccine composition of any one of embodiments 1 to 13, wherein the composition comprises about $1 \times 10^5$ to about $1 \times 10^8$ cancer cells.
15. The cancer vaccine composition of any one of embodiments 1 to 14, wherein the DNA of the cancer cells comprises modified guanine bases.
16. The cancer vaccine composition of any one of embodiments 1 to 15, wherein the composition further comprises an adjuvant.
17. The cancer vaccine composition of embodiment 16, wherein the adjuvant modifies monocyte function.
18. The cancer vaccine composition of embodiment 16, wherein the adjuvant comprises aluminum hydroxide.
19. The cancer vaccine composition of embodiment 16, wherein the adjuvant comprises CLDC.
20. The cancer vaccine composition of embodiment 16, wherein the adjuvant comprises poly IC, CpG oligodeoxynucleotides (ODN), or imiquimod.
21. The cancer vaccine composition of embodiment 16, wherein the adjuvant comprises liposomes.
22. The cancer vaccine composition of embodiment 21, wherein the liposomes are conjugated to an agonist.
23. The cancer vaccine composition of embodiment 22, wherein the agonist is an agonist of at least one of TLR3 and TLR9.
24. The cancer vaccine composition of any one of embodiments 1 to 23, wherein the composition further comprises a pharmaceutically acceptable carrier.
25. The cancer vaccine composition of embodiment 24, wherein the pharmaceutically acceptable carrier is normal saline, dextrose saline, or phosphate buffered saline.
26. The cancer vaccine composition of any one of embodiments 1 to 25, wherein the cancer cells are inactivated using light treatment.
27. The cancer vaccine composition of embodiment 26, wherein the light treatment lasts for about 1 minute to about 3 minutes.
28. The cancer vaccine composition of embodiment 26 or 27, wherein the light treatment does not substantially alter the structure of the antigenic proteins on the cancer cells.

29. The cancer vaccine composition of any one of embodiments 26 to 28, wherein the light treatment alters the DNA of the cancer cells.

30. The cancer vaccine composition of embodiment 29, wherein the light treatment selectively oxidizes guanine bases in the DNA of the cancer cells.

31. The cancer vaccine composition of any one of embodiments 26 to 30, wherein the light treatment does not substantially change the metabolic processes, phenotype, or structure of the cancer cells.

32. The cancer vaccine composition of any one of embodiments 26 to 31, wherein the light treatment does not substantially change surface marker expression or activity in the cancer cells.

33. The cancer vaccine composition of embodiment 32, wherein the light treatment does not change expression levels of EpCAM, CD38, CD34, CD117, CD44, CD24, Sca1, HLA, Glut1, MHC Class I, PDL-L1, CD45, gp70, GFP or CD90 in the cells.

34. The cancer vaccine composition of any one of embodiments 26 to 33, wherein the light treatment does not compromise the cell membrane or nuclear membrane integrity of the cells.

35. The cancer vaccine composition of any one of embodiments 26 to 34, wherein the light treatment comprises treatment with UV light.

36. The cancer vaccine composition of embodiment 35, wherein the UV light has a wavelength of 170 to 400 nm.

37. The cancer vaccine composition of embodiment 35, wherein the UV light has a wavelength of 315 to 400 nm.

38. The cancer vaccine composition of embodiment 35, wherein the UV light has a wavelength of 310 to 320 nm.

39. The cancer vaccine composition of embodiment 35, wherein the UV light has a wavelength of 280 to 360 nm.

40. The cancer vaccine composition of embodiment 35, wherein the UV light has a wavelength of 280 to 315 nm.

41. The cancer vaccine composition of embodiment 35, wherein the UV light has a wavelength of 180 to 280 nm.

42. The cancer vaccine composition of embodiment 35, wherein the UV light has a wavelength of 170 to 200 nm.

43. The cancer vaccine composition of any one of embodiments 35 to 42, wherein the dose of UV light is about 200 Joules to about 600 Joules.

44. The cancer vaccine composition of embodiment 43, wherein the dose of UV light is about 200 Joules to 400 Joules.

45. The cancer vaccine composition of embodiment 44, wherein the dose of UV light is about 300 Joules.

46. The cancer vaccine composition of any one of embodiments 26 to 45, wherein the light treatment is performed by contacting the cancer cells with light in the presence of a photosensitizer.

47. The cancer vaccine composition of embodiment 46, wherein the concentration of the photosensitizer is about 1 μM to about 50 μM.

48. The cancer vaccine composition of embodiment 46 or 47, wherein the concentration of the photosensitizer is less than about 10 μM.

49. The cancer vaccine composition of any one of embodiments 46 to 48, wherein the photosensitizer is riboflavin.

50. A method for treating cancer in a patient in need thereof, the method comprising administering the cancer vaccine composition of any one of embodiments 1 to 49 to the patient.

51. The method of embodiment 50, wherein the cancer vaccine composition is administered simultaneously or sequentially with a vaccine-enhancing agent.

52. The method of embodiment 51, wherein the vaccine-enhancing agent is an angiotensin receptor blocker (ARB) or a beta blocker (BB).

53. The method of embodiment 51 or 52, wherein the vaccine-enhancing agent is losartan.

54. The method of embodiment 53, wherein the dose of losartan is between about 5 and about 100 mg/kg.

55. The method of embodiment 54, wherein the dose of losartan is about 60 mg/kg.

56. The method of embodiment 51 or 52, wherein the vaccine-enhancing agent is propranolol.

57. The method of any one of embodiments 50 to 56, wherein the cancer vaccine composition is administered once to the patient.

58. The method of one of embodiments 50 to 56, wherein the cancer vaccine composition is administered more than once to the patient.

59. The method of embodiment 58, wherein the cancer vaccine composition is administered 2, 3, 4, 5, 6, 7, 8, 9, or 10 times to the patient.

60. The method of embodiment 58 or 59, wherein the cancer vaccine composition is administered to the patient at least once every 7 days.

61. The method of embodiment 58 or 59, wherein the cancer vaccine composition is administered to the patient at least once every 14 days.

62. The method of embodiment 58 or 59, wherein the cancer vaccine composition is administered to the patient at least once every 6 months.

63. The method of any one of embodiments 50 to 62, wherein the cancer vaccine composition is administered by a route selected from subcutaneous, intramuscular, intravenous, intranasal, sublingual, buccal, inhaled, intradermal, intratumoral, intra-organ, oral, and intraperitoneal.

64. The method of embodiment 63, wherein the cancer vaccine composition is administered by subcutaneous injection.

65. The method of embodiment 63, wherein the cancer vaccine composition is administered by intravenous injection.

66. The method of embodiment 63, wherein the cancer vaccine composition is administered by intramuscular injection.

67. The method of any one of embodiments 50 to 62, wherein the patient is immunocompetent.

68. The method of any one of embodiments 50 to 62, wherein the patient is immunocompromised.

69. The method of any one of embodiments 50 to 68, wherein the treatment reduces tumor growth by at least 10% compared to tumor growth in an unvaccinated patient.

70. The method of embodiment 69, wherein the treatment reduces tumor growth by at least 20% compared to tumor growth in an unvaccinated patient.

71. The method of embodiment 70, wherein the treatment reduces tumor growth by at least 50% compared to tumor growth in an unvaccinated patient.

72. The method of any one of embodiments 50 to 71, wherein the treatment prolongs survival of the patient by at least 10% compared to an unvaccinated patient.

73. The method of embodiment 72, wherein the treatment prolongs survival of the patient by at least 20% compared to an unvaccinated patient.

74. The method of embodiment 73, wherein the treatment prolongs survival of the patient by at least 50% compared to an unvaccinated patient.

75. The method of any one of embodiments 50 to 74, wherein the treatment upregulates IgG and/or IgM in the patient.

76. The method of any one of embodiments 50 to 75, wherein the treatment activates T-cells in the patient.

77. The method of any one of embodiments 50 to 76, wherein the cancer is breast cancer, lung cancer, liver cancer, bladder cancer, gynecological cancer, brain cancer, stomach cancer, prostate cancer, skin cancer, thyroid cancer, pancreatic cancer, colon cancer, or blood cancer.

78. The method of embodiment 77, wherein the skin cancer is a melanoma.

79. The method of embodiment 77, wherein the blood cancer is a leukemia, a lymphoma, or a myeloma.

80. The method of embodiment 79, wherein the leukemia is Acute Lymphocytic Leukemia or Acute Myeloid Leukemia.

81. The method of embodiment 79, wherein the lymphoma is Hodgkin's Lymphoma or Non-Hodgkin's Lymphoma.

82. The method of embodiment 79, wherein the myeloma is multiple myeloma.

83. The method of any one of embodiments 50 to 82, wherein the cancer is metastatic cancer.

84. The method of any one of embodiments 50 to 83, wherein the cancer vaccine composition is administered to the patient in combination with one or more additional therapies.

85. The method of embodiment 84, wherein the one or more additional therapies are selected from the group consisting of checkpoint inhibitors, antibody therapies, genetically engineered dendritic cells, genetically engineered T-cells, and chemotherapy.

86. A method for producing a cancer vaccine, the method comprising contacting cancer cells with UV light in the presence of riboflavin.

87. The method of embodiment 86, wherein the UV light alters the DNA of the cancer cells.

88. The method of embodiment 87, wherein the UV light selectively oxidizes guanine bases in the DNA of the cancer cells.

89. The method of embodiment 86, wherein the light treatment does not substantially alter the structure of the antigenic proteins on the cancer cells.

90. The method of any one of embodiments 86 to 89, wherein the UV light does not substantially change the metabolic processes, phenotype, or structure of the cancer cells.

91. The method of any one of embodiments 86 to 90, wherein the UV light does not substantially change surface marker expression or activity in the cancer cells.

92. The method of embodiment 91, wherein the UV light does not substantially change expression levels of EpCAM, CD38, CD34, CD117, CD44, CD24, Sca1, HLA, Glut1, MHC Class I, PDL-L1, CD45, gp70, GFP and/or CD90 in the cells.

93. The method of any one of embodiments 86 to 92, wherein the inactivation does not compromise the cell membrane and nuclear membrane integrity of the cells.

94. The method of any one of embodiments 86 to 93, wherein the cancer cells are contacted with UV light in the presence of riboflavin for about 1 minute to about 3 minutes.

95. The method of any one of embodiments 86 to 94, wherein the UV light has a wavelength of 170 to 400 nm.

96. The method of any one of embodiments 86 to 94, wherein the UV light has a wavelength of 315 to 400 nm.

97. The method of any one of embodiments 86 to 94, wherein the UV light has a wavelength of 310 to 320 nm.

98. The method of any one of embodiments 86 to 94, wherein the UV light has a wavelength of 280 to 360 nm.

99. The method of any one of embodiments 86 to 94, wherein the UV light has a wavelength of 280 to 315 nm.

100. The method of any one of embodiments 86 to 94, wherein the UV light has a wavelength of 180 to 280 nm.

101. The method of any one of embodiments 86 to 94, wherein the UV light has a wavelength of 170 to 200 nm.

102. The method of any one of embodiments 86 to 101, wherein the dose of UV light is about 200 Joules to about 600 Joules.

103. The method of embodiment 102, wherein the dose of UV light is about 200 Joules to about 400 Joules.

104. The method of embodiment 103, wherein the dose of UV light is about 300 Joules.

105. The method of any one of embodiments 86 to 104, wherein the cancer cells are in a single-cell suspension.

106. The method of embodiment 105, wherein the riboflavin is added to the single-cell suspension.

107. The method of any one of embodiments 86 to 106, wherein the cancer cells are preincubated in a solution containing riboflavin before contacting the cells with the UV light.

108. The method of embodiment 107, wherein the solution comprises 10 to 100 µM riboflavin.

109. The method of embodiment 107, wherein the solution comprises about 1 µM to about 50 µM riboflavin.

110. The method of embodiment 107, wherein the solution comprises less than about 10 µM riboflavin.

111. The cancer vaccine composition of any one of embodiments 1 to 49 for use as a medicament.

112. The cancer vaccine composition of any one of embodiments 1 to 49 for use as a medicament for treating cancer.

113. The cancer vaccine composition of any one of embodiments 1 to 49 for use in a method of treating cancer.

114. Use of the cancer vaccine composition of any one of embodiments 1 to 49 in the manufacture of a medicament for treating cancer.

115. The cancer vaccine composition of any one of embodiments 111 to 113, or the use of embodiment 114, wherein the cancer is breast cancer, lung cancer, liver cancer, bladder cancer, gynecological cancer, brain cancer, stomach cancer, prostate cancer, skin cancer, thyroid cancer, pancreatic cancer, colon cancer, or blood cancer.

116. The cancer vaccine composition or use of embodiment 115, wherein the skin cancer is a melanoma.

117. The cancer vaccine composition or use of embodiment 115, wherein the blood cancer is a leukemia, a lymphoma, or a myeloma.

118. The cancer vaccine composition or use of embodiment 117, wherein the leukemia is Acute Lymphocytic Leukemia or Acute Myeloid Leukemia.

119. The cancer vaccine composition or use of embodiment 117, wherein the lymphoma is Hodgkin's Lymphoma or Non-Hodgkin's Lymphoma.

120. The cancer vaccine composition or use of embodiment 117, wherein the myeloma is multiple myeloma.

121. The cancer vaccine composition of any one of embodiments 111 to 113, or the use of embodiment 114, wherein the cancer is metastatic cancer.

EXAMPLES

The following examples, which are included herein for illustration purposes only, are not intended to be limiting.

Example 1. Inactivation of Tumor Cells Derived from a Tumor Cell Line

CAMA cells, a human mammary tumor line, were inactivated using UV light treatment in the presence of riboflavin. Cells were treated using the Mirasol® PRT Illumination device, at 10% (190 Joules), 20% (380 Joules), 30% (570 Joules), 40% (760 Joules), 50% (950 Joules) or 100% (1896 Joules) illumination intensities. Cells that were not treated with UV light (Live) were included as a control. Proliferation (FIG. 1), viability (FIG. 2), cell surface marker expression (FIG. 3, FIG. 4, FIG. 5), caspase activity (FIG. 6), and cell membrane and nuclear membrane integrity were examined the day of (day 0) and 2, 4, 6, and 8 days after treatment.

Figure 2:
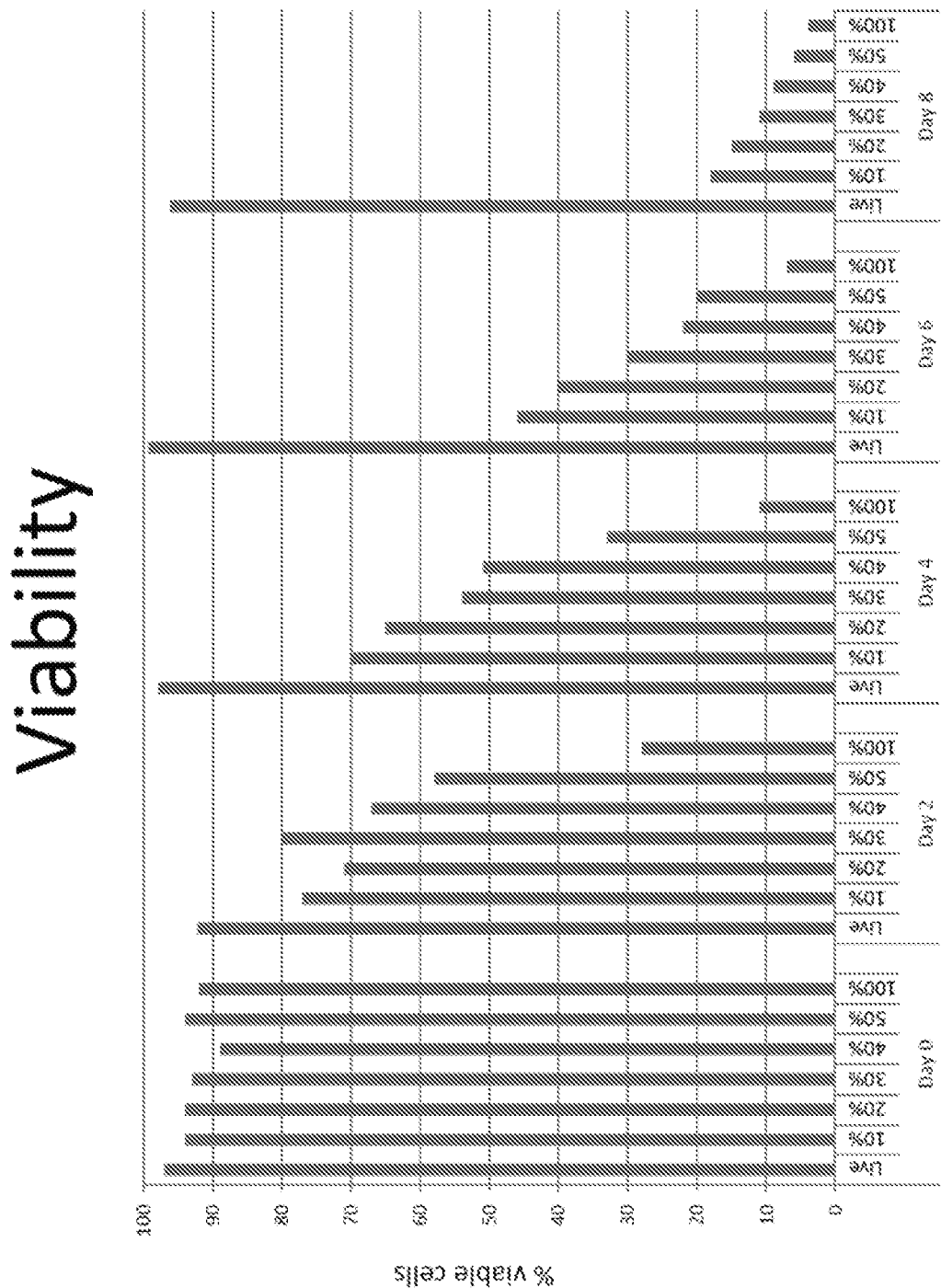
FIG. 2 shows viability of CAMA cells after treatment with riboflavin and UV light.
Figure 3:
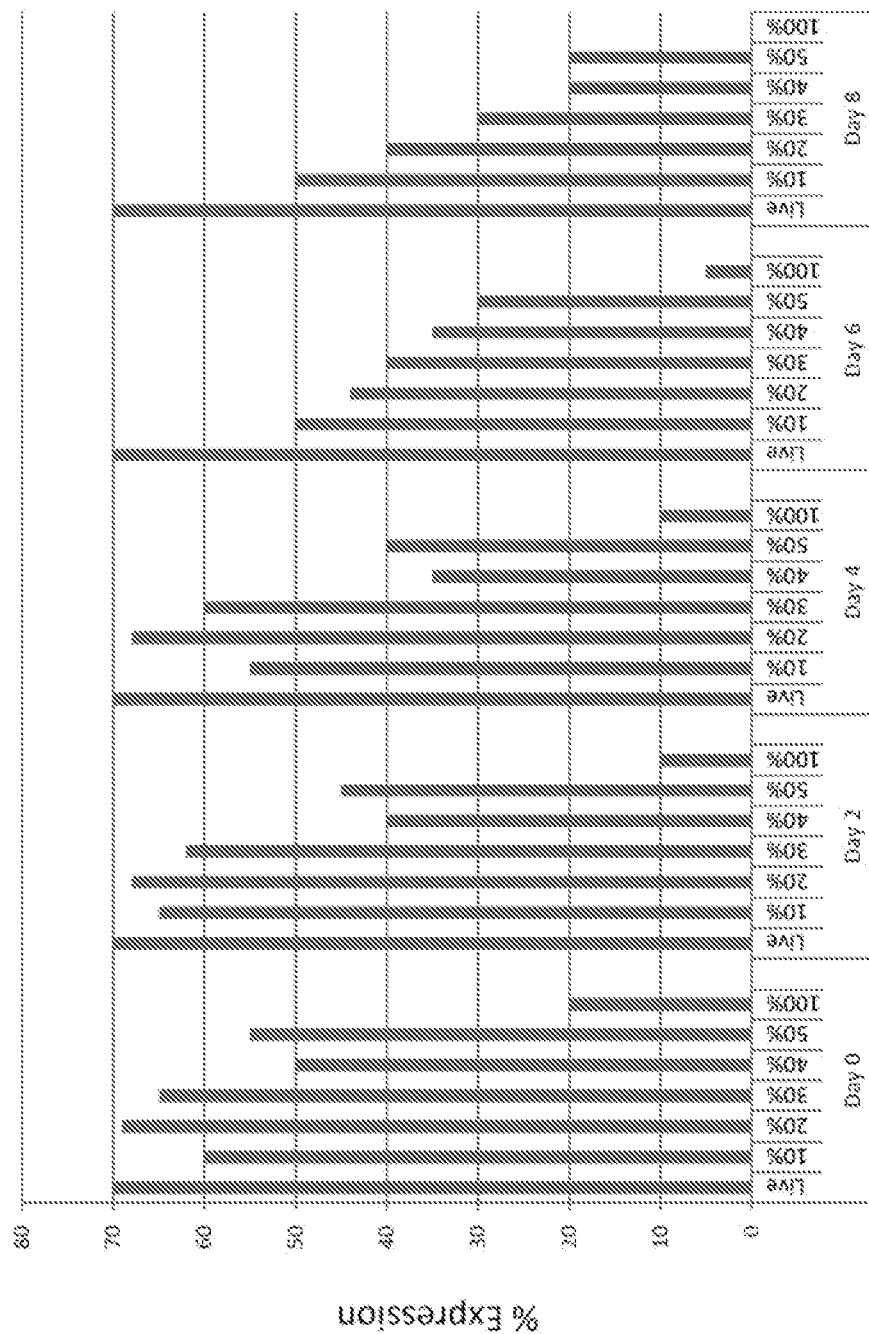
FIG. 3 shows expression of EpCAM, a surface marker, in CAMA cells after treatment with riboflavin and UV light.
Figure 4:
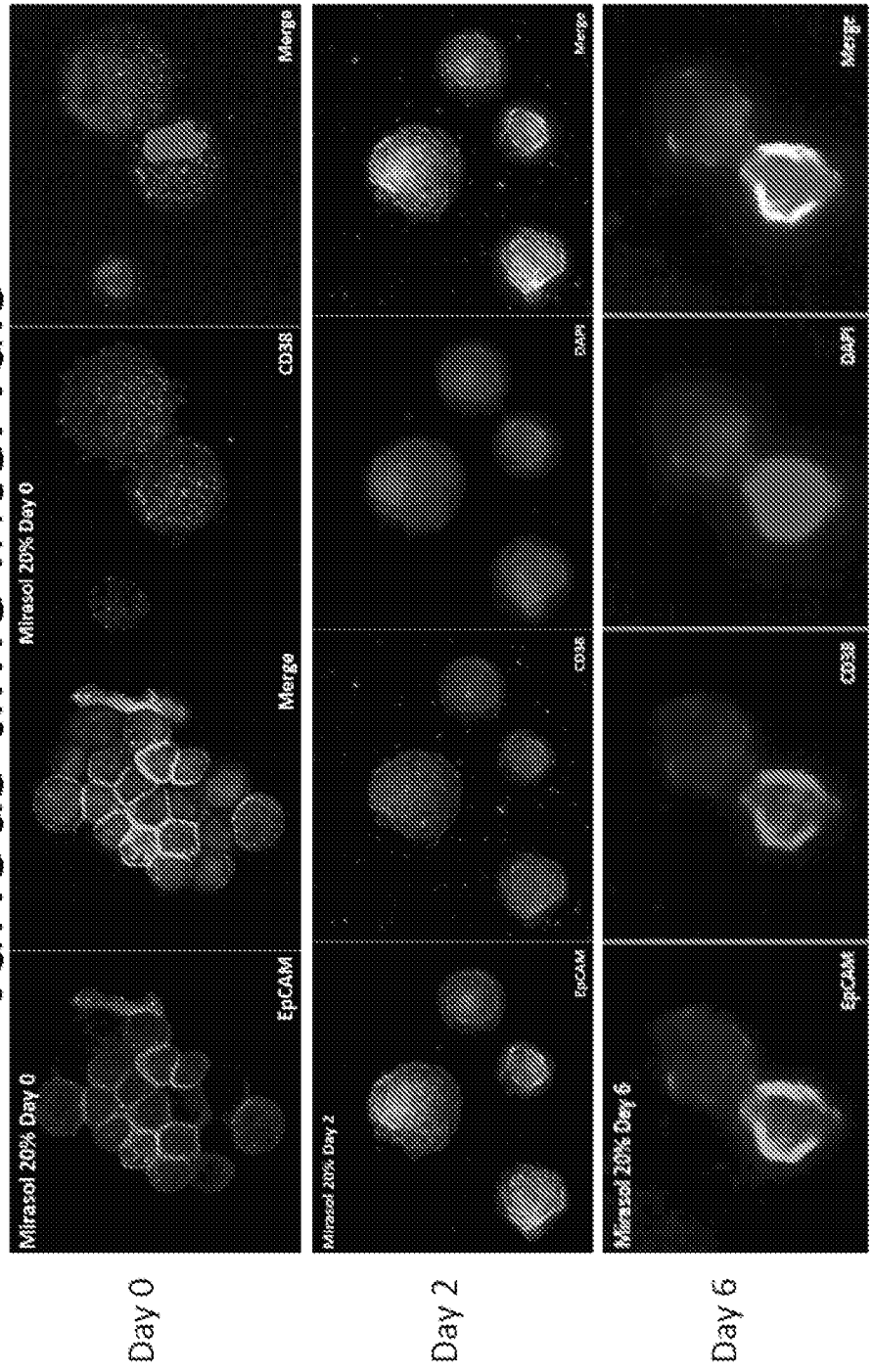
FIG. 4 provides fluorescence microscopy images comparing surface marker expression on CAMA cells at various time intervals post-treatment with riboflavin and UV light (20% illumination intensity).

As shown in FIG. 1, treatment with riboflavin/UV light rendered the cells unable to replicate in culture. This effect was seen immediately, on the day of treatment, even at doses as low as 190-380 Joules (10-20% illumination intensity). Even though they had been inactivated, the cells remained substantially viable after treatment (FIG. 3). Specifically, the cells remained intact and metabolically functional (FIG. 4). After four days, the concentration of caspase-3 increased significantly (FIG. 6), consistent with cell death by an apoptotic mechanism. Thus, after treatment, the cells no longer proliferate and slowly die off over time.

Figure 5:
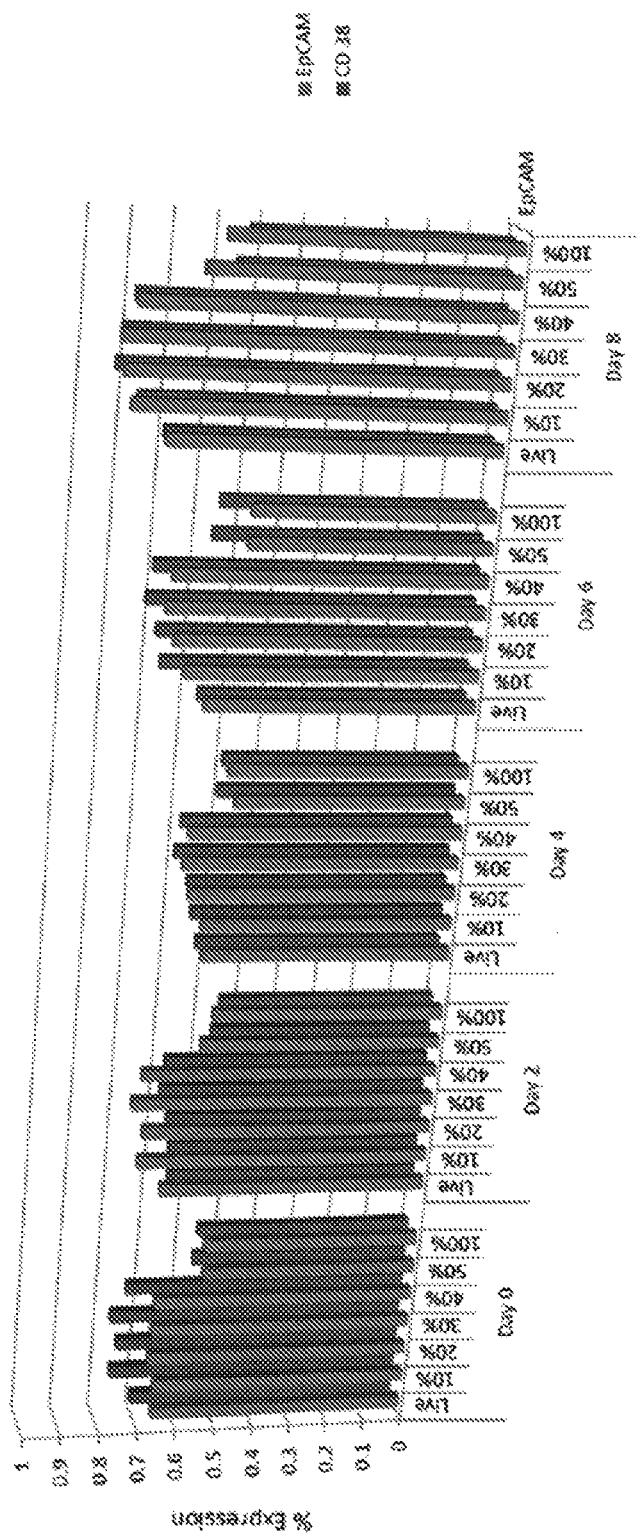
FIG. 5 shows relative expression of surface markers EpCAM (front row of bars) and CD38 (back row of bars) within the viable cell population after treatment with varying doses of UV light.
Figure 6:
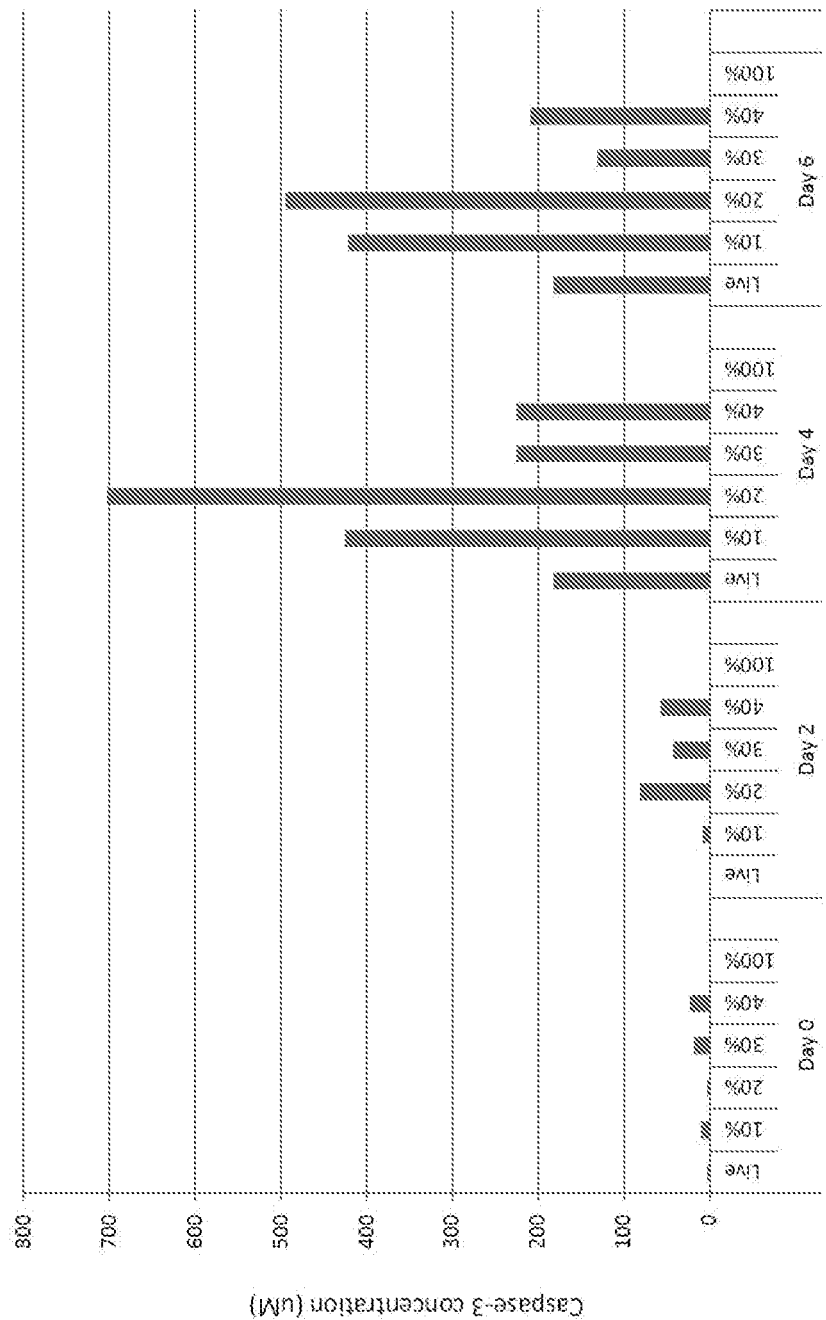
FIG. 6 shows Caspase-3 concentration in CAMA cells after treatment with riboflavin and UV light.
Figure 7:
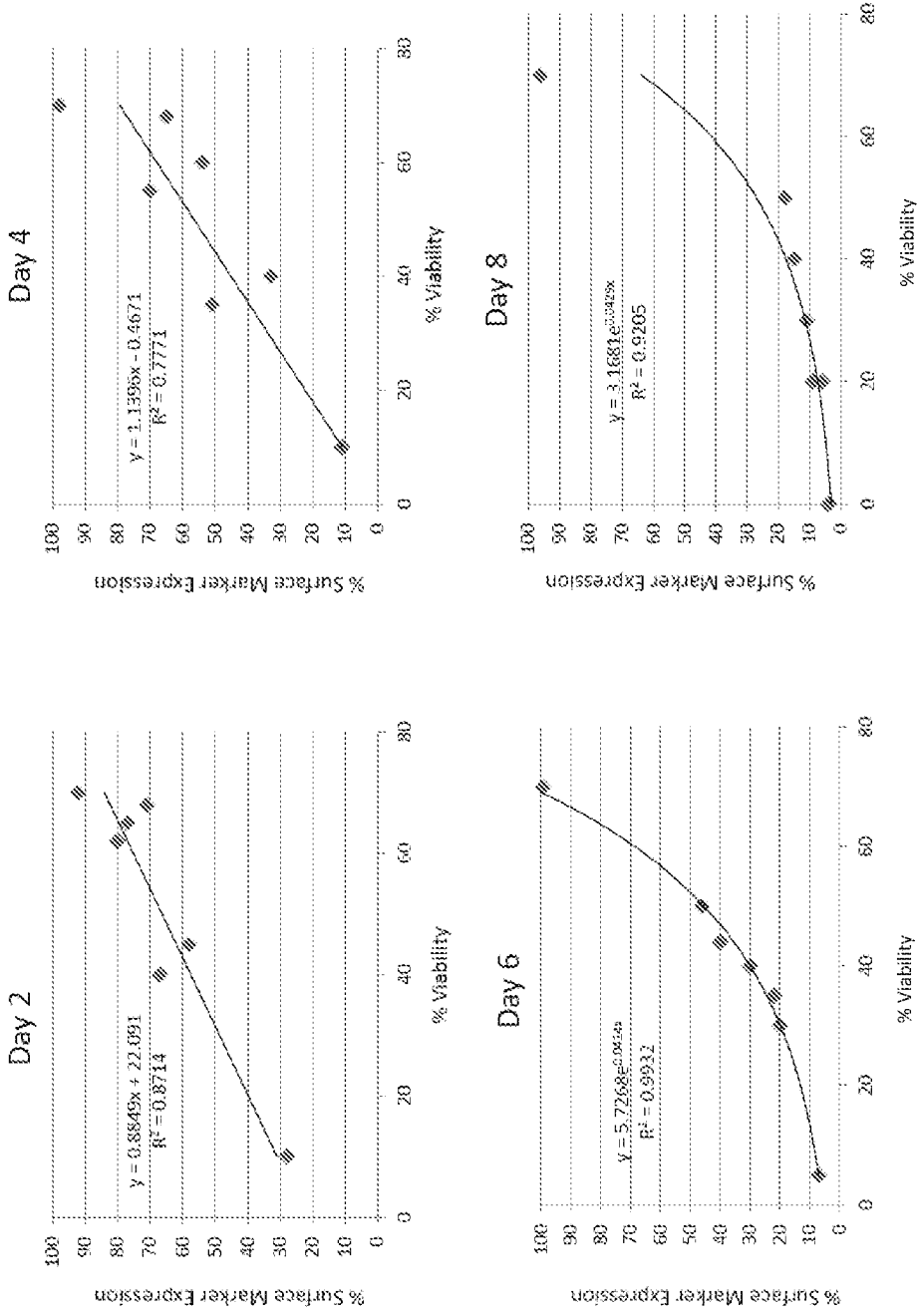
FIG. 7 depicts the correlation between surface marker expression and viability of CAMA cells after treatment with riboflavin and UV light.

Cell surface marker expression (EpCAM and CD38) was maintained at relatively consistent level after treatment, from doses as low as 190-380 Joules (10-20% illumination intensity) to doses as high as 1896 Joules (100% illumination intensity) (FIG. 3, FIG. 5). Cell viability was positively correlated with surface marker expression (FIG. 7). This indicates that the cells maintained the cell surface antigens required to generate an immune response after UV treatment, even over a wide range of UV doses.

This data establishes a dynamic therapeutic range for preparing inactivated cells without damaging the cell surface marker proteins needed to stimulate antibody generation.

Example 2. Vaccine Safety: Inactivation of Autologous Tumor Cells and Injection into Healthy Test Mice PyMT tumor cells were injected into wildtype C57Bl6 mice. After tumors grew, tumor tissue was harvested to generate a cancer cell vaccine. A total of $2\times10^8$ PyMT ex vivo tumor cells collected from seven C57Bl6 mice were resuspended in solution comprising (i) 265 mls of DMEM media supplemented with 20% fetal bovine serum and glutamine (no antibiotics) and (ii) 35 mls of riboflavin. The cells were treated with UV light at a dose of 300 Joules in total.

$1\times10^6$ of the treated cells were placed in culture media and incubated under optimum conditions. No evidence of growth or proliferation was observed after a month in culture, consistent with 100% inactivation of the replication potential for the treated cells.

Additionally, a total of 10 C57/Bl6 mice were injected subcutaneously with $1\times10^6$ inactivated cells. Additional doses were administered one, two and three weeks later (total of 4 doses, $1\times10^6$ cells each dose). The animals were monitored for 160 days after the first injection. No tumors were observed in any test subject during the 160-day monitoring period, and no side effects of injection were observed, consistent with complete inactivation of the cells.

Lastly, 8 immune deficient NOD/SCID mice were injected with $1\times10^6$ inactivated PyMT cells in the flank. The animals were monitored for 5 months after injection. No tumor growth was observed during this monitoring period.

Taken together, these data suggest that there are no safety concerns for the injected cell preparation.

Example 3. Vaccine Efficacy: Injection of Inactivated Tumor Cells into Test Mice with Breast Cancer Inhibits Tumor Growth C5761/6 mice were injected with $2.5\times10^5$ viable PyMT cells in the mammary fat pad. Three days later, mice were treated with either saline (control, n=10), vaccine with the inactivated tumor cells (n=10), or a previously-studied lysate vaccine (positive control, n=6). The vaccine comprised $1\times10^6$ inactivated cells per mouse, co-mixed with the CLDC adjuvant system (lipids+TLR agonists) and was administered subcutaneously into both forelimbs under anesthesia (typically 100-110 µl/limb). The mice also received losartan (60 mg/kg) by intraperitoneal injection once a day for three days, for a total of three doses starting on the day the vaccine was given. Finally, mice received a CLDC adjuvant booster (100 µl, i.p.) 24 hours after the vaccine was given. Vaccination was repeated weekly for a total of 5 vaccine/losartan/CLDC booster cycles. Tumor growth over time was measured using a caliper (length× width). The extent of mortality seen over a 2 month period post-injection was also monitored.

Figure 8:
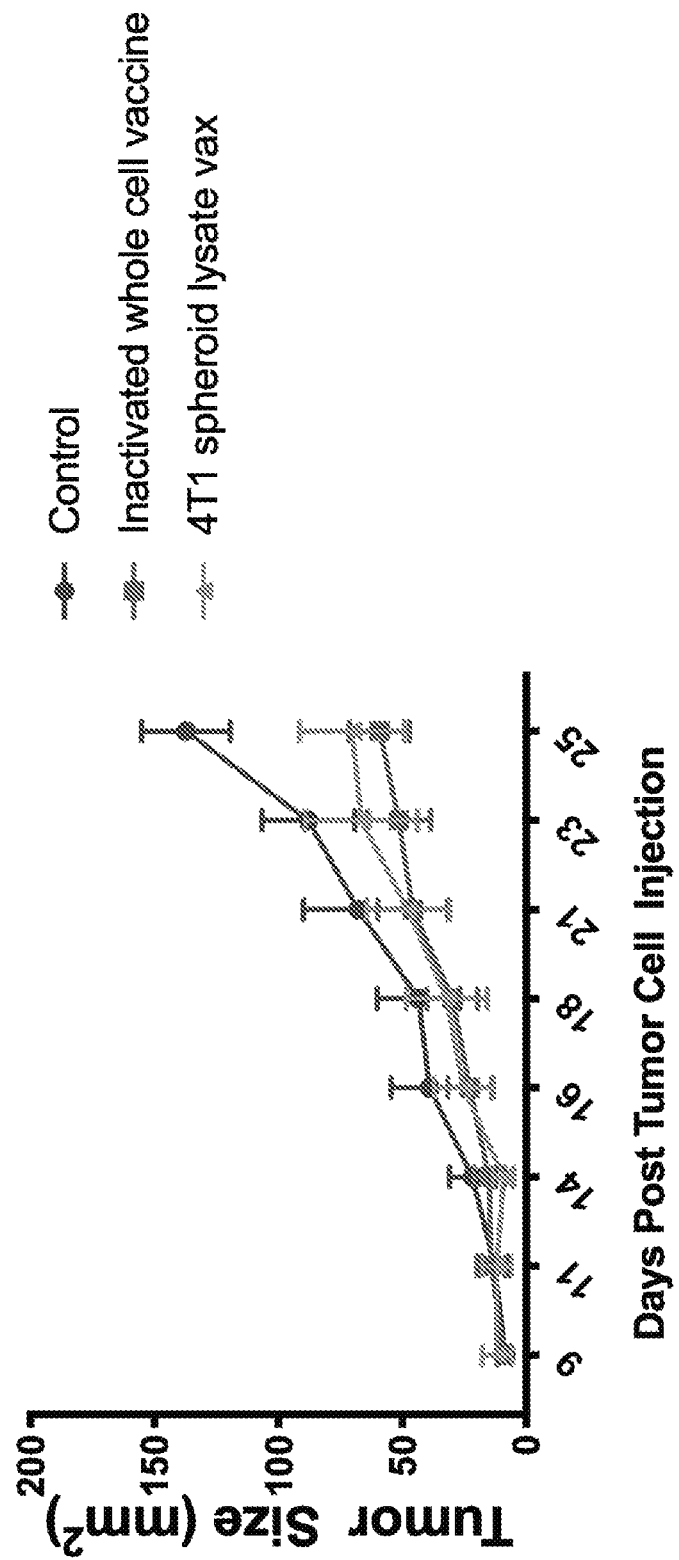
FIG. 8 shows tumor growth curves for mice bearing PyMT breast carcinoma tumors that were injected with saline (control, no vaccine) compared to those receiving inactivated whole cell vaccine and those receiving a lysate vaccine (4T1 Spheroid Lysate Vax, as described in WO 2016/161309, which is incorporated herein by reference in its entirety). Results indicated a statistically significant reduction in tumor cell growth observed for the inactivated whole cell vaccine versus untreated control group, starting at Day 23 post injection ($p=0.02$ at day 23 and $p<0.001$ at day 25).

FIG. 8 shows tumor growth curves for saline-injected (control, no vaccine) compared to those receiving inactivated whole cell vaccine and those receiving the lysate vaccine (4T1 Spheroid Lysate Vax). A statistically significant reduction in tumor cell growth was observed for the inactivated whole cell vaccine group versus the untreated control group, starting at Day 23 post injection (p=0.02 at day 23 and p<0.0001 at day 25).

Figure 9:
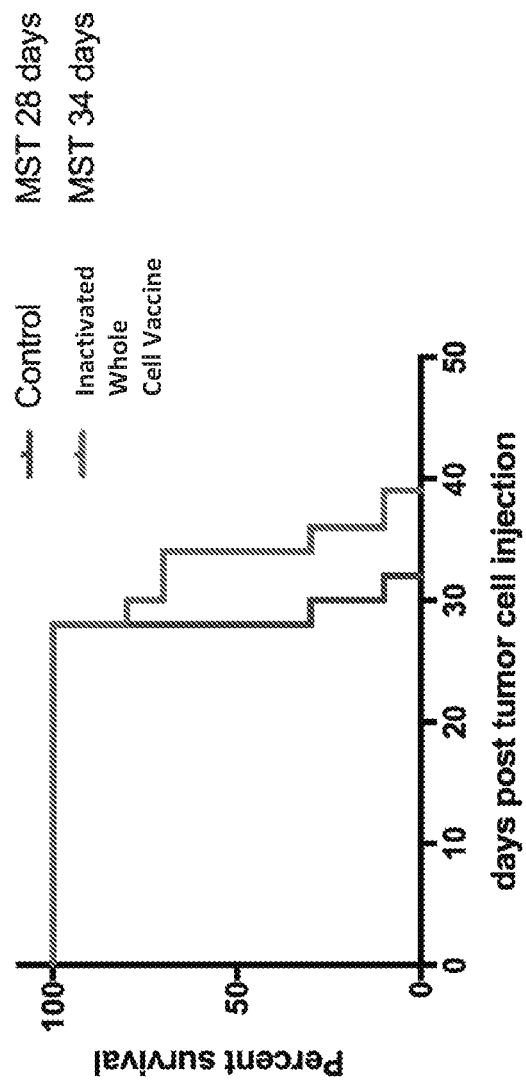
FIG. 9 shows overall survival in vaccinated (inactivated whole cell vaccine) versus untreated/saline (control) groups of mice bearing PyMT tumors. The mice receiving the inactivated whole cell vaccine had a significantly extended survival time ($p=0.009$, Mantel-Cox Log Rank test) as compared to the saline-treated control group.

FIG. 9 shows overall survival. In this experiment, mice were euthanized when the longest tumor diameter exceeded 15 mm. Mice receiving the inactivated whole cell vaccine had a significantly extended survival time (p=0.0038) as compared to the saline-treated control group. The overall median survival time of mice receiving inactivated whole cell vaccine was 34 days compared to control at 26 days (~30% increase).

Figure 14:
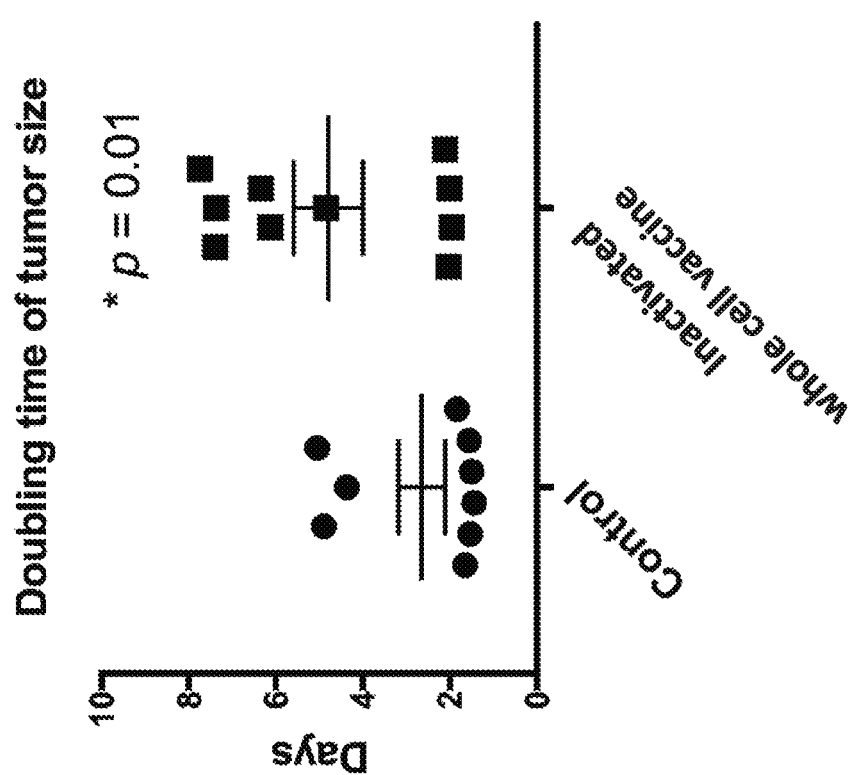
FIG. 14 is a graph showing doubling time of tumor size, as described in Example 3. Doubling time was greater in mice treated with inactivated whole cell vaccine (p=0.01).

FIG. 14 shows doubling time. Doubling time of tumor growth was significantly greater in the mice treated with the inactivated whole cell vaccine as compared to control mice (p=0.01).

Figure 10:
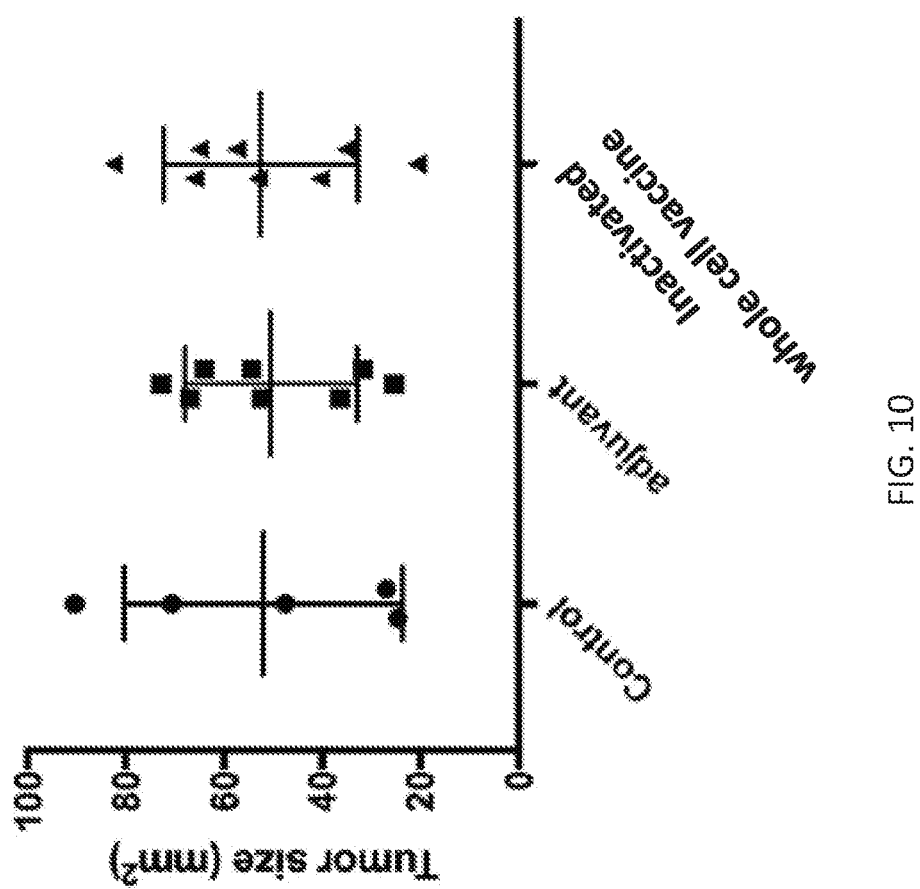
FIG. 10 shows the size of 4T1 tumors in mice, prior to surgical removal. Following surgery, mice were arranged into the 3 groups shown so that each group had a similar average tumor size ($p=0.9$) and spread. PBS ("control"), n=5 mice; Adjuvant, n=8 mice; inactivated whole cell vaccine, n=8 mice.

Example 4. Vaccine Efficacy: Injection of Inactivated Tumor Cells into Test Mice with Aggressive Breast Cancer Reduces Lung Metastasis, Limits Tumor Regrowth and Increases Survival The 4T1 mammary carcinoma is a transplantable tumor cell line that is highly tumorigenic and invasive and, unlike most tumor models, can spontaneously metastasize from the primary tumor in the mammary gland to multiple distant sites including lymph nodes, blood, liver, lung, brain and bone. Balb/c mice were injected with $1\times10^6$ 4T1-luciferase tumor cells in the mammary fat pad. 11 days after injection (when the average tumor area was 52 mm²), the primary tumors were measured and then surgically removed. One mouse died during the procedure. The remaining 21 mice were grouped according to pre-surgical tumor size such that the average tumor size was equal (FIG. 10). The following groups were determined: PBS ("control"), n=5 mice; Adjuvant, n=8 mice; inactivated whole cell vaccine, n=8 mice.

Surgically removed tumor tissue was then placed in media at 4° C. overnight. The following day, the tumor tissue was minced and then treated with collagenase. Cells were filtered to remove tissue debris and then quantitated. A portion of the cells was used to create the first vaccine. Mice were vaccinated once a week with the inactivated 4T1 tumor cells ($1.7 \times 10^6$ cells)+adjuvant, boosted with adjuvant 24 hrs after vaccination, and provided 3 daily doses of 60 mg/kg losartan starting the day the vaccine was given. This cycle was repeated weekly.

Figure 11A:
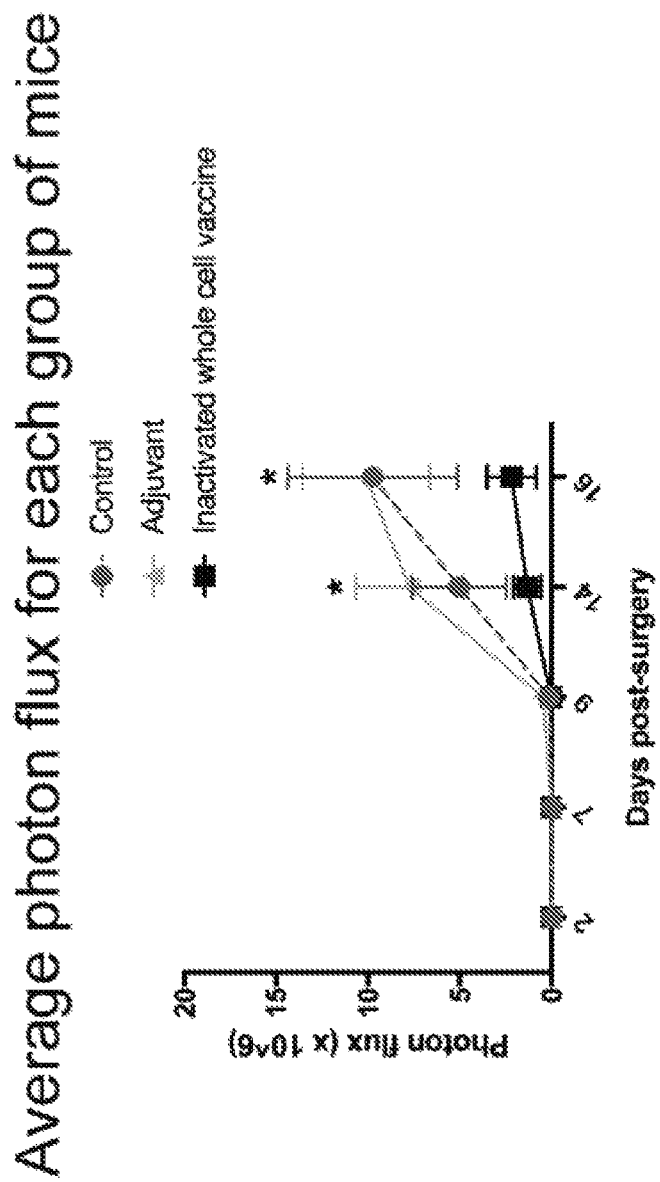
FIG. 11A and FIG. 11B show the results of an experiment wherein mice were treated with PBS (Control), with losartan and cationic liposome-DNA complexes (CLDC) (Adjuvant), or with the inactivated whole cell vaccine (Adjuvant+vaccine) weekly starting 24 hours after surgical removal of the primary tumor. Metastatic disease in the lungs was quantitated using IVIS imaging following i.p. injection of 100 µl of luciferin.
Figure 11B:
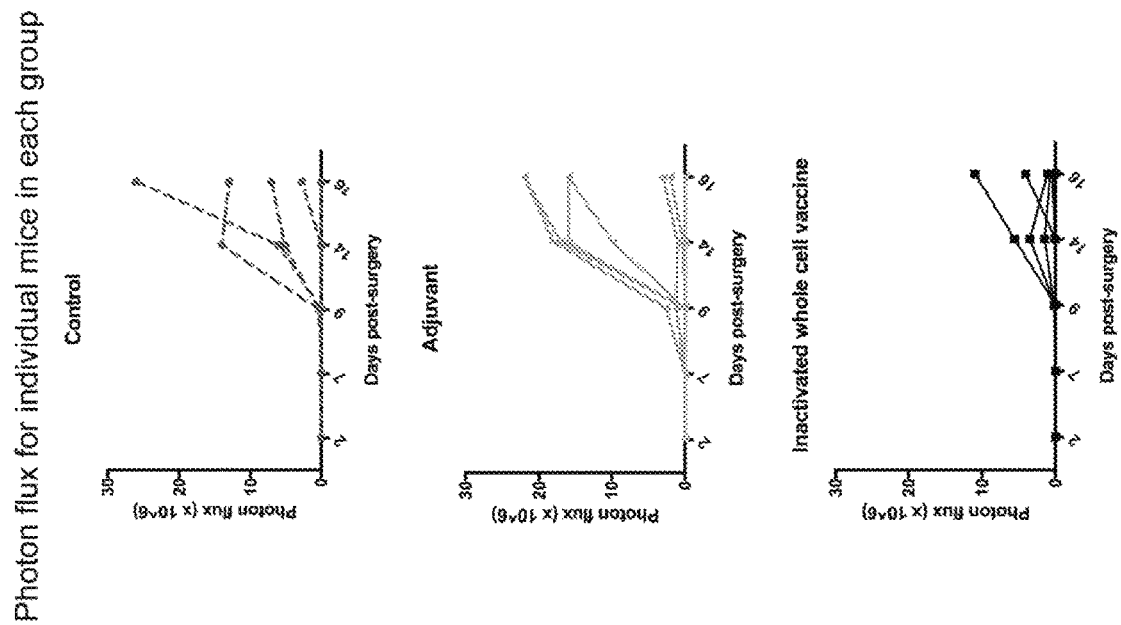

Mice were imaged using an IVIS machine on a regular basis to detect metastatic disease development. Mice were injected with 100 μl luciferin, then put on the IVIS 10 minutes later. Photon flux numbers were calculated using the IVIS-based software and compared between groups (FIG. 11A-B).

Mice were treated with PBS only (Control), with cationic liposome-DNA complexes (CLDC) and losartan (Adjuvant), or with the inactivated whole cell vaccine (Adjuvant+vaccine) weekly starting 24 hours after surgical removal of the primary tumor. Metastatic disease in the lungs was quantitated using IVIS imaging (FIG. 19) following i.p. injection of 100 μl of luciferin. As shown in FIG. 11A, there was a significant decrease in measured metastatic burden in mice treated with the vaccine compared to adjuvant treated mice (Day 14, p=0.0157) and compared to both the control mice and adjuvant treated mice (Day 16, p=0.0119 and p=0.0021, respectively). FIG. 11B shows the photon flux data over time of the individual mice in each group.

Figure 12:
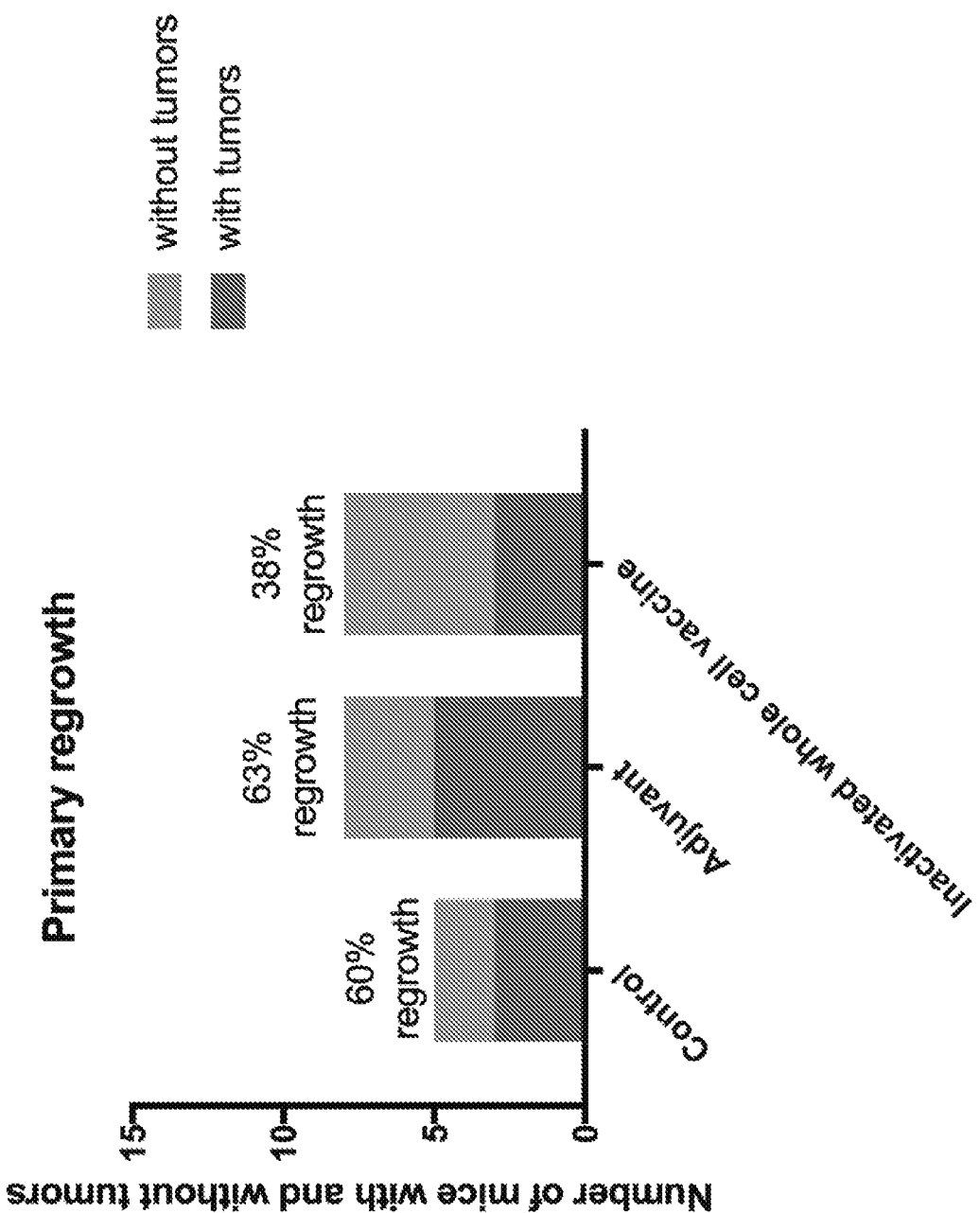
FIG. 12 shows the frequency of regrowth of the primary tumor due to incomplete removal of the primary tumor in the various treatment groups.

In some mice, there was regrowth of the primary tumors due to incomplete excision. The number of mice with primary regrowth 17 days after surgery was documented (FIG. 12). Interestingly, less mice treated with the inactivated whole cell vaccine had regrowth of their primary tumor compared to the other treatment groups. In the control, 60% of the mice had regrowth of the primary tumor, 63% in the adjuvant only group, and only 38% in the inactivated whole cell vaccine group.

Figure 13:
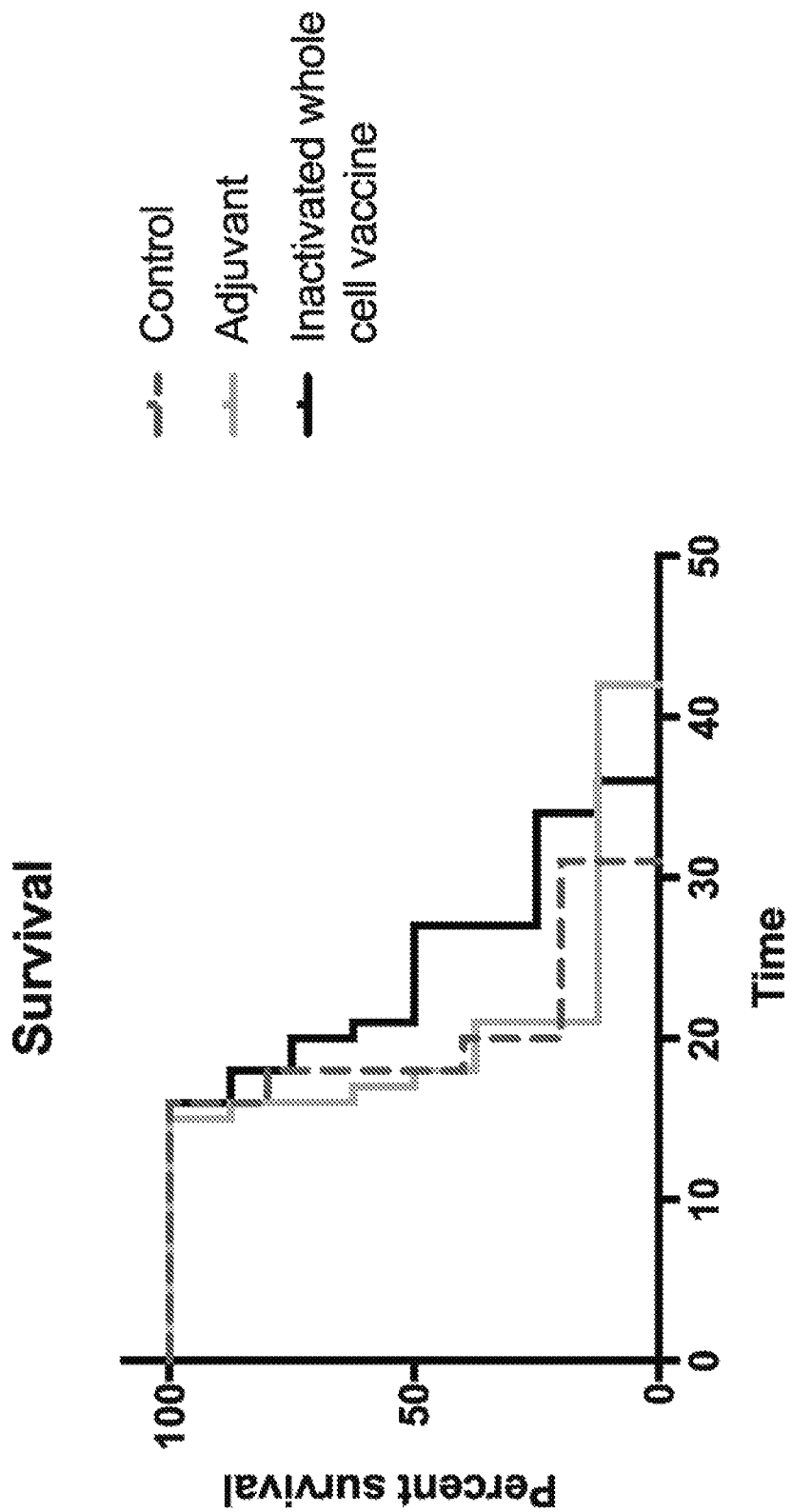
FIG. 13 is a survival curve showing that survival of the mice was enhanced in the group that received the inactivated whole cell vaccine. Mice were euthanized when moribund (i.e. weight loss >10%, seizures, decreased mobility, unkempt appearance, etc.). The median survival of the control and adjuvant group was 17.5 days while the inactivated whole cell vaccine treated group was 24 days. This difference in survival was not statistically significant (p=0.1), but biologically relevant given the aggressive nature of the 4T1 tumor.

The effect of the vaccine on survival was also tested. Mice were euthanized when they displayed signs of morbidity (decreased weight by 10% or greater, poor mobility, seizures, etc.) and day post-surgery was evaluated (FIG. 13). Median survival time of mice treated with inactivated whole cell vaccine was 24 days compared to 18 days for the control mice, and 17.5 days post-surgical removal of the primary tumor for the adjuvant only mice. Thus, treatment with the vaccine increased median survival by about 6 days. All mice did eventually succumb to metastatic disease in all groups. The 4T1 metastatic model is extremely aggressive and typically unresponsive to many conventional therapies, so any observed effect is noteworthy.

Example 5. Testing Efficacy of the Inactivated Whole Cell Vaccine in a Different Mouse Tumor Model (LLC)

To test the efficacy of the inactivated whole cell vaccine in a different mouse tumor model, healthy B6 mice were injected with Lewis Lung Carcinoma (LLC) cells. When primary tumors grow, they were excised and the tumor cells were inactivated with 300J. Another 19 B6 mice were injected with $5 \times 10^5$ LLC cells subcutaneously in the flank. Three days after tumor cell injection, mice received their first vaccine of $1.7 \times 10^6$ inactivated cells per mouse per vaccine. They also received the CLDC adjuvant, including losartan and the 24 hour post-vaccine CLDC booster. Mice received their vaccines weekly for a total of three vaccines. Mice were all euthanized on day 19 and tumor tissue was collected and stained for immune cells.

Figure 15:
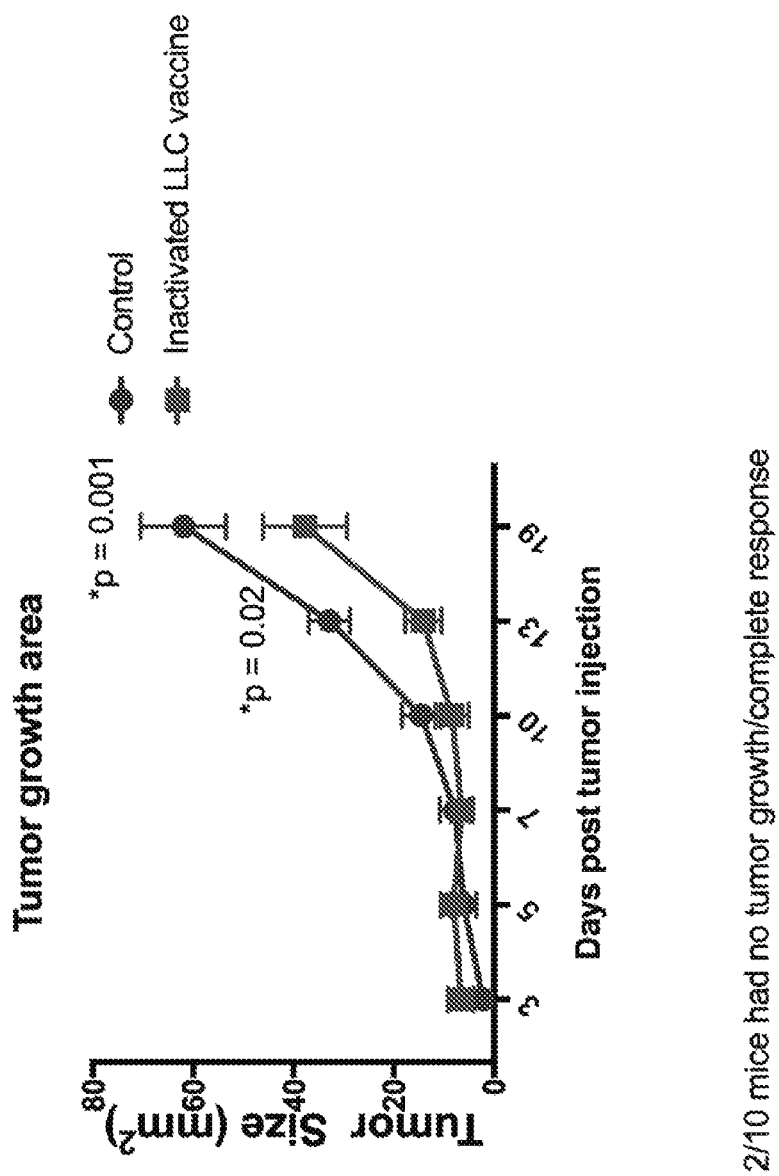
FIG. 15 is a graph showing tumor growth area at 3, 5, 7, 10, 13, and 19 days post tumor injection of mice bearing subcutaneous Lewis Lung Carcinoma tumors (LLC) and treated with either PBS control or inactivated LLC vaccine. Tumor growth was significantly reduced in mice vaccinated with the inactivated LLC vaccine at 13 (p=0.02) and 19 (p=0.001) days post tumor cell injection.
Figure 16:
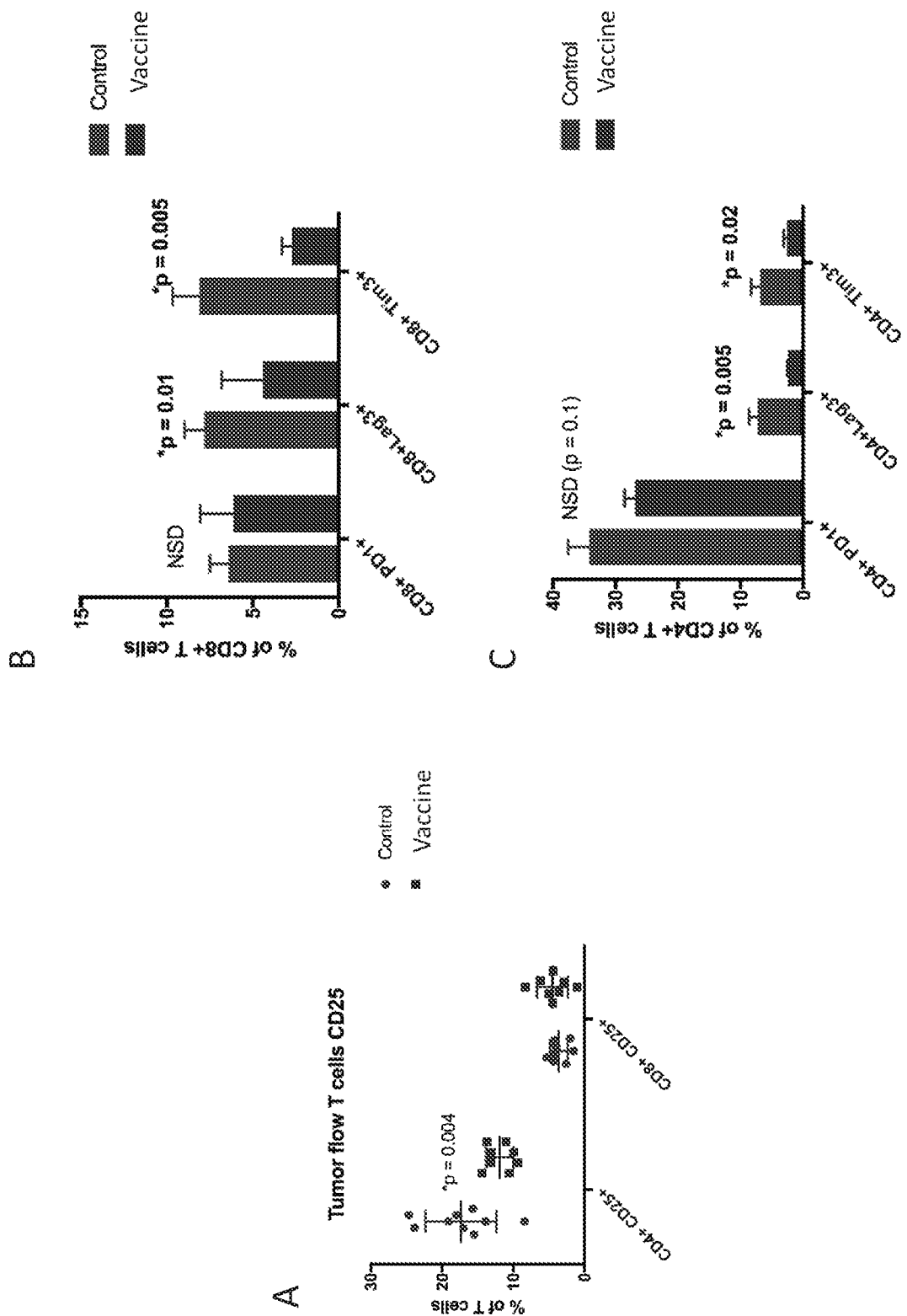
FIG. 16A-C are graphs showing subtypes of T cells in tumors obtained from control and vaccinated mice from the LLC study.

As shown in FIG. 15, tumor growth was significantly decreased/delayed in the inactivated whole cell vaccine treated mice (p=0.02 on day 13 and p=0.001 on day 19). Two of the mice in the vaccine treated group did not have tumors on day 19 (Complete response=20%). The final tumor weights of the mice that had tumors was decreased in the vaccine treated mice, although not significantly (p=0.0547). The tumor doubling time was also not significantly decreased, but was less in the vaccine treated mice (p=0.0570). In the tumors, there was a significant decrease in CD4+CD25+ T cells in the vaccinated mice (p=0.004, putative immune suppressive T regulatory cells) as well as a decrease in CD4+ T cells expressing GITR (p=0.02), another marker of T-regulatory cells (FIG. 16A). Relatedly, there was a significant decrease in CD8+ T cells expressing the immune suppressive proteins Lag3 (p=0.01) and Tim3 (p=0.05) (FIG. 16B) and a significant decrease in CD4+ T cells expressing the proteins Lag3 (p=0.005) and Tim3 (p=0.02) (FIG. 16C) in the vaccinated mice tumors.

Example 6. Determining Whether Ex Vivo Canine Tumor Tissue Contains Tumor Cells that Maintain Surface Expression of Proteins Two tumor tissues were surgically obtained from dogs with spontaneous cancer undergoing treatment. One tissue was from an anal gland adenocarcinoma (ASA) and the other from a thyroid carcinoma (TC). Tissue was collagenase digested and the single cell suspension obtained was frozen in multiple vials at −80° C. Tumor cells were later thawed and one bullet of cells was used as control cells and the other as the inactivated cells. The canine cells were inactivated using 300J. The cell numbers used were less than that previously used for inactivating tumor cells. It took 1 minute and 38 seconds to inactivate each group of cells. The tumor cells were then stained for canine CD44, CD90, PD-L1 and CD45 expression. CD45 was used to gate out all hematopoetic cells (FIG. 25A-D). Analysis of the "tumor" cells was done on CD45 negative cells (including tumor cells, fibroblasts, endothelial cells, and other cell types).

For the ASA, 1 hr after inactivation, 15% of the cells expressed CD44 (compared to 20% of control), 1% expressed CD90 (compared to 0.3%) and 7.7% expressed PD-L1 (compared to 3.1%). For TC, after inactivation, 7.1% expressed CD44 (compared to 6.8% of control cells), 0.6% expressed CD90 (compared to 0.4%) and 0% expressed PD-L1 (compared to 0.2%). The remaining cells were placed at 4° C. for 48 hours and then stained again. After 48 hours, for ASA: CD44=10% (11% control), CD90=2% (3.2% control), PD-L1=9.5% (3% control). For TC: CD44=5.8% (8.9% control), CD90=3.1% (3.2% control) and PD-L1=3% (2.9% control).

Figures 26A, 26B, 26C, 26D:
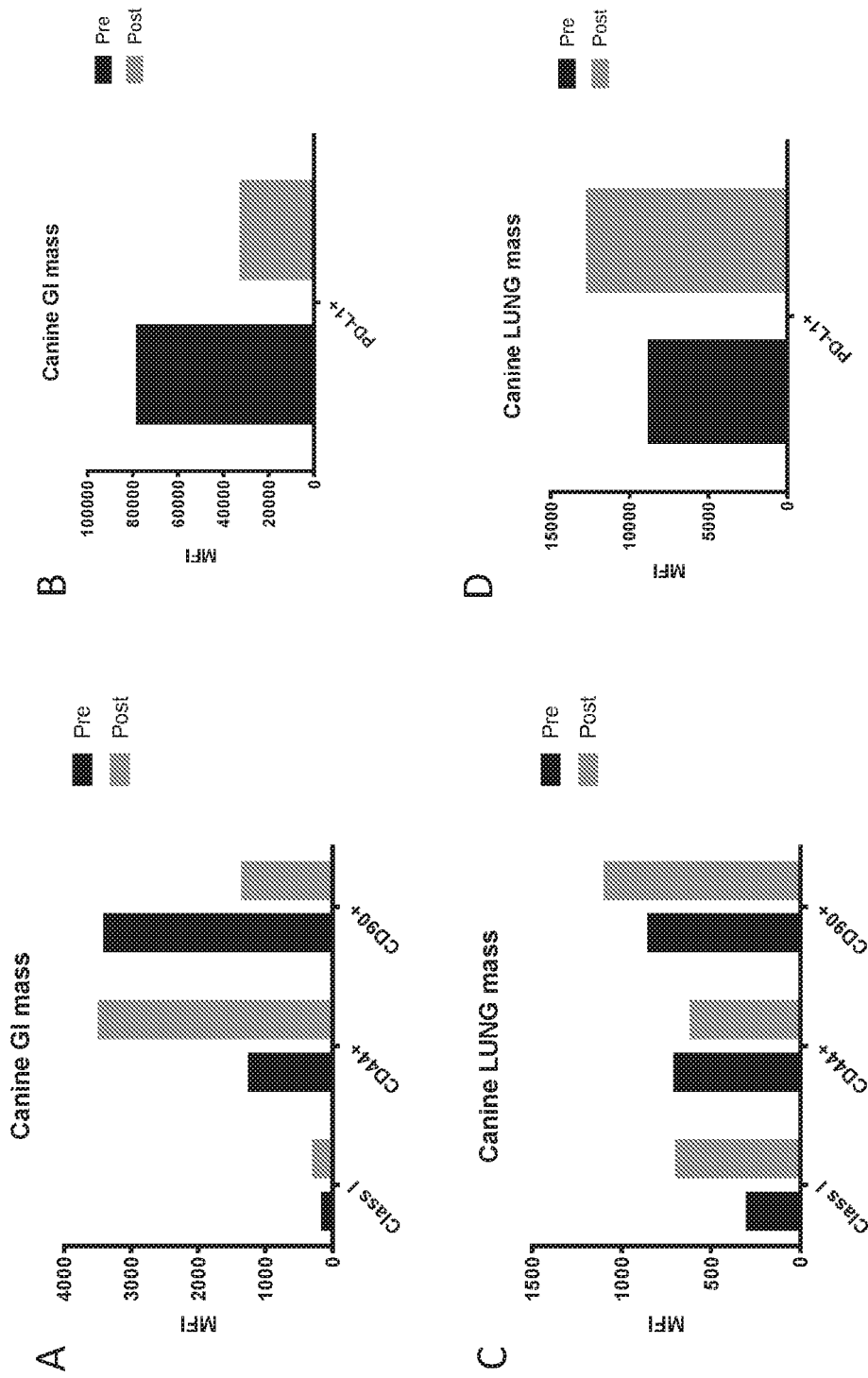
FIG. 26A-D shows UV+RF inactivation of two additional ex vivo canine tumor tissues.

Additional pieces of other tumor tissue were obtained from two different dogs undergoing surgery. One was a GI mass and the other was a lung mass. The tumor tissue was digested using collagenase, washed and then strained to make a single cell suspension. The cells were then all frozen in cell freezing media. Later, cells were thawed and half of the cells were inactivated using a UV+RF (UV light+riboflavin) protocol. The other half were kept on ice. The cells were then stained for surface expression of canine MHC Class I, CD44, CD90, and PD-L1 (FIG. 26).

Taken together, these data indicate that the surface markers are maintained on ex vivo canine tumor cells following inactivation.

Figure 17:
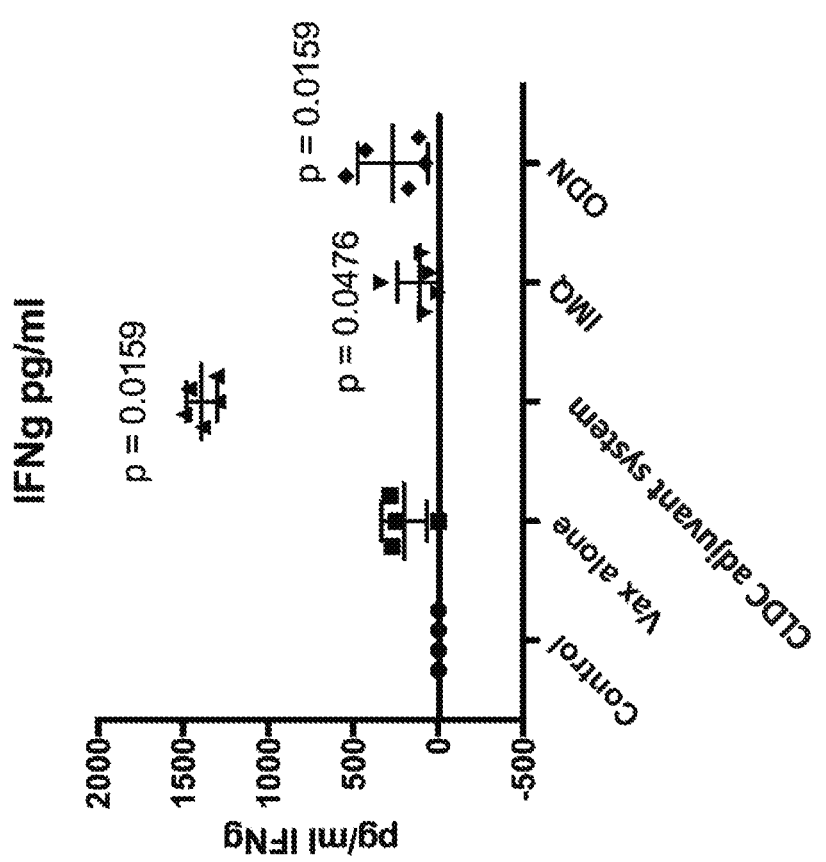
FIG. 17 shows production of IFNg (pg/ml) after spleen cells were isolated from healthy, naïve B6 mice, which were vaccinated and boosted with the inactivated whole cell vaccine (derived from 4T1 mouse tumor cells) with various immune adjuvants. The spleen cells were then restimulated with inactivated 4T1 tumor cells in vitro for 72 hours and IFNg was measured via ELISA. The CLDC adjuvant system produced the best IFNg response.

Example 7. Testing Different Adjuvants to Produce a Significant Cellular and Humoral Immune Response Against Inactivated Tumor Cells Healthy Balb/c mice were either vaccinated with PBS or inactivated cells alone, or vaccinated with the inactivated 4T1 vaccine (used in the metastatic mouse tumor study described in Example 4) with either the CLDC adjuvant system, topical imiquimod applied to the skin prior to vaccination (2 mg/kg), or admixed with CpG ODN (50 µg per vaccine). The vaccines were given s.c. in equal volumes in both the left and right forelimb of the mice, close to the foot. Mice received $1.7 \times 10^6$ cells per mouse per vaccine. Vaccines were given on day 1 and then again on day 14. Mice were euthanized 8 days after the booster vaccine was given and spleen and blood were collected. Spleen cells were cultured with inactivated 4T1 cells (to prevent replication) and IFNg production was measured after 72 hours (FIG. 17). Spleen cells were cultured at a ratio of 25 spleen cells to 1 inactivated 4T1 cell.

As shown in FIG. 17, the CLDC adjuvant system had the best recall response in terms of IFNg production. This was followed by CpG ODN. The vaccine alone also produced some level of IFNg in 3 of the 4 mice, but there was no significant difference compared to control.

Example 8. Further Testing Adjuvants to Produce a Significant Cellular and Humoral Immune Response Against Inactivated Tumor Cells Healthy Balb/c mice were either vaccinated with PBS, inactivated cells alone or vaccinated with the inactivated 4T1 vaccine (used in the metastatic mouse tumor study described in Example 4) with either the CLDC adjuvant system, topical imiquimod applied to the skin prior to vaccination (2 mg/kg), or admixed with CpG ODN (50 µg per vaccine). The vaccines were given subcutaneously in equal volumes in both the left and right forelimb of the mice, close to the foot. Mice received $1.7 \times 10^6$ cells per mouse per vaccine. Vaccines were given on day 1 and then again on day 14. Mice were euthanized 8 days after the booster vaccine was given and spleen and blood was collected. The serum from these mice was screened against live 4T1 tumor cells for IgG antibody binding by incubating serum with the cells at either a 1:500 or a 1:1000 dilution, staining with a fluorescently-labeled donkey anti-mouse secondary antibody, then subtracting out the background staining (normal mouse serum at 1:500 and 1:1000).

Figure 18:
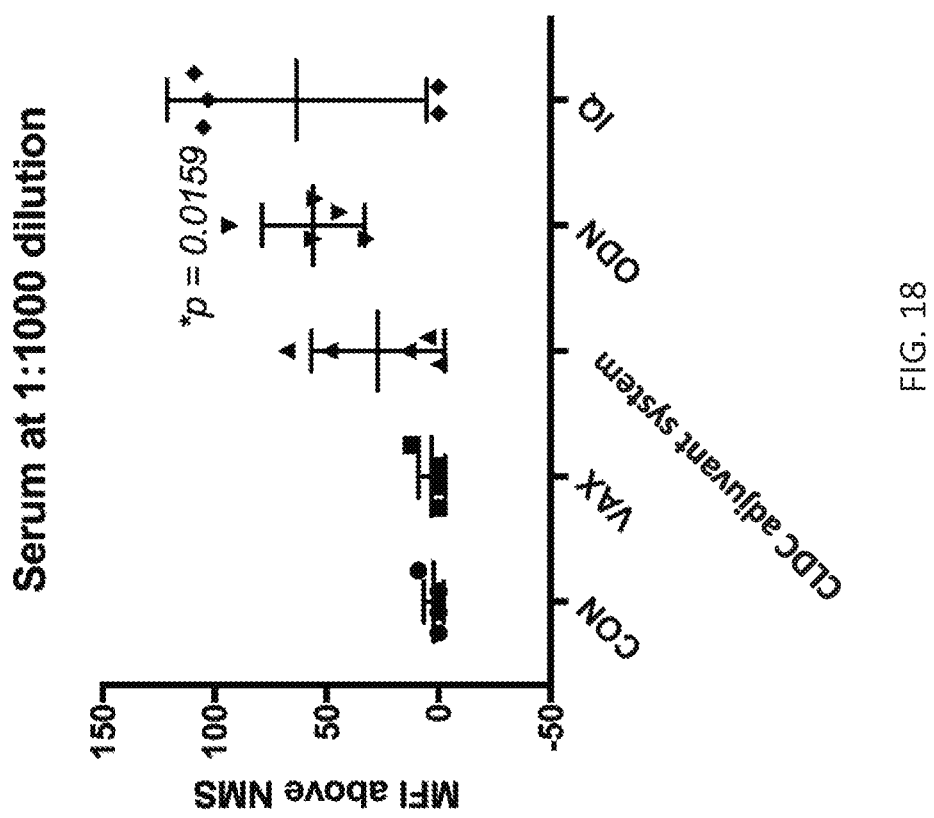
FIG. 18 shows mean fluorescent intensity (MFI) of serum IgG antibodies at a 1:1000 dilution, derived from the blood of mice shown in FIG. 17, binding to live 4T1 cells. All of the vaccine/adjuvant systems produced significantly higher binding than control or inactivated cells alone.

As shown in FIG. 18, unvaccinated and inactivated whole cell vaccine alone did not produce any IgG specific for 4T1 tumor cells. Imiquimod produced variable amounts with 3 of the 5 mice having very high staining. CpG ODN produced a reliable and significant increase in staining at 1:1000 dilution. Not very much staining above background was detected at a 1:500 dilution.

Example 9. Preservation of Surface Antigens

Figures 21A, 21B:
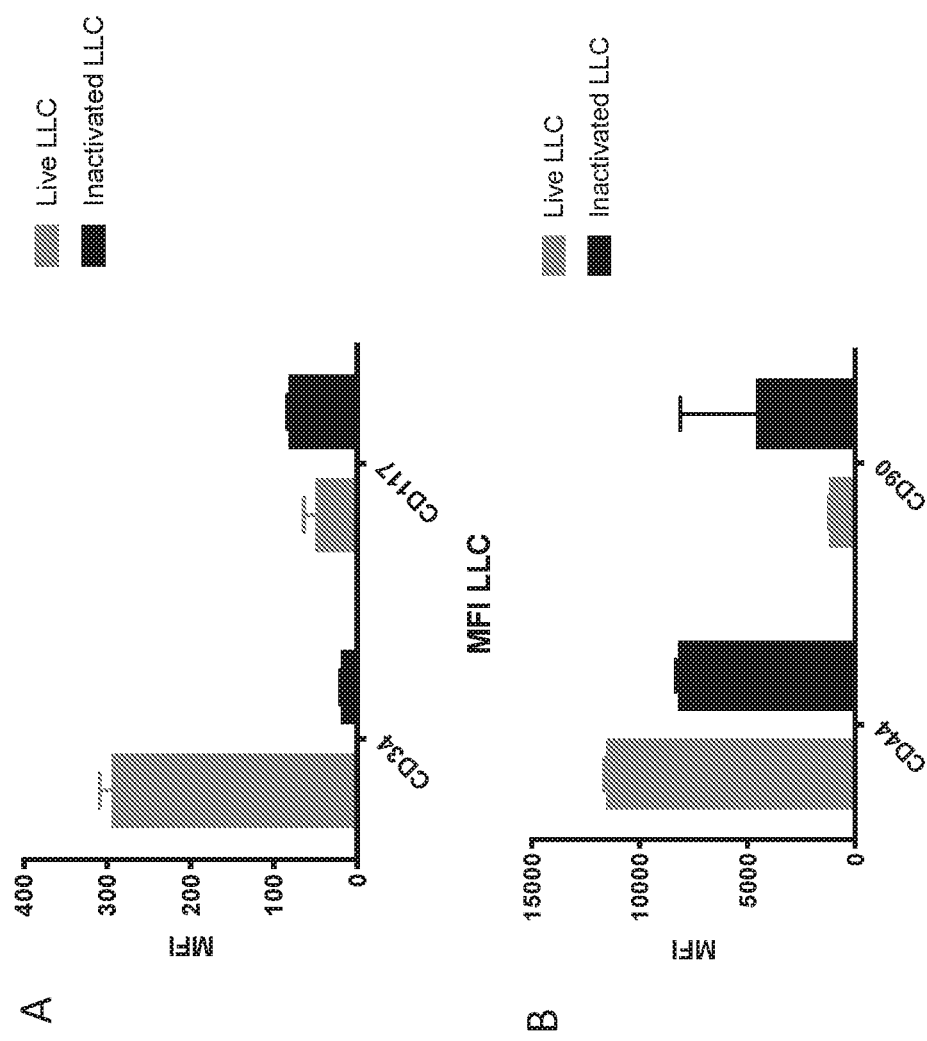
FIG. 21A-21B shows cell surface staining of mouse LLC cells following UV+Rf (UV light+Riboflavin) inactivation.
Figure 22:
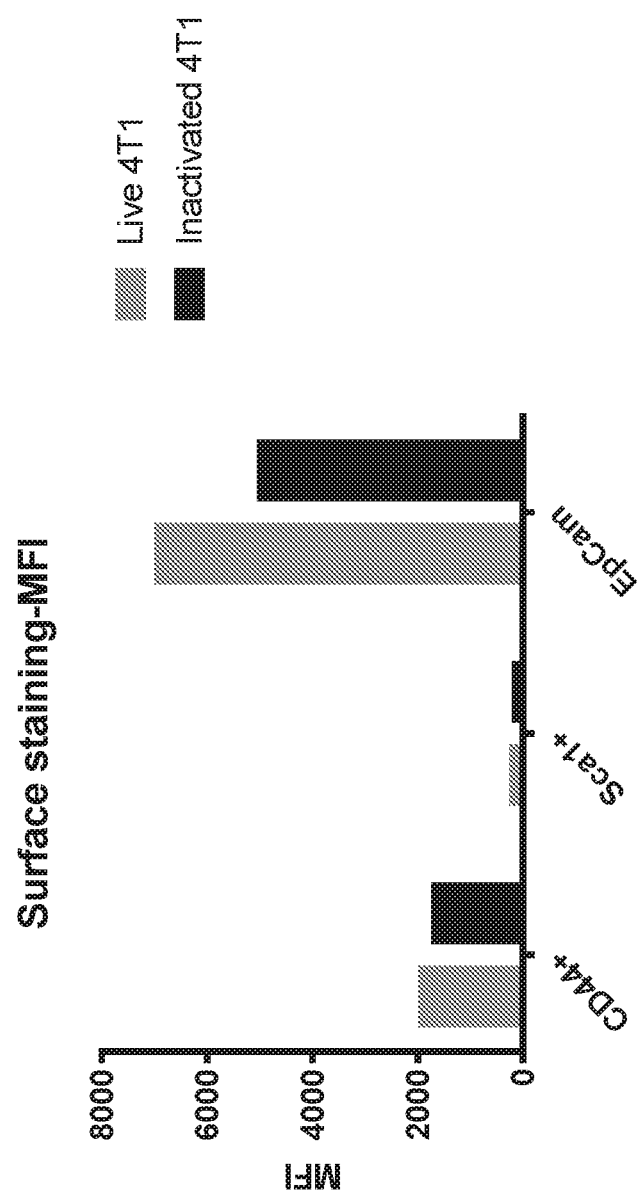
FIG. 22 shows surface staining of the mouse 4T1 breast carcinoma cells following UV+Rf inactivation.

The mouse lung carcinoma line, LLC, maintained expression of surface antigens following inactivation (FIG. 21A-21B). LLC cells were treated with riboflavin (RF, 50 µM) and UV light (300J) and stained for surface expression of CD34, CD117, CD44 and CD90. All 4 antigens were maintained on the surface of the cells. The mouse breast carcinoma cell line, 4T1, was also assessed for surface marker expression of CD44, Sca1, and EpCAM before and after UV+RF inactivation (FIG. 22).

Figures 23A, 23B, 23C, 23D:
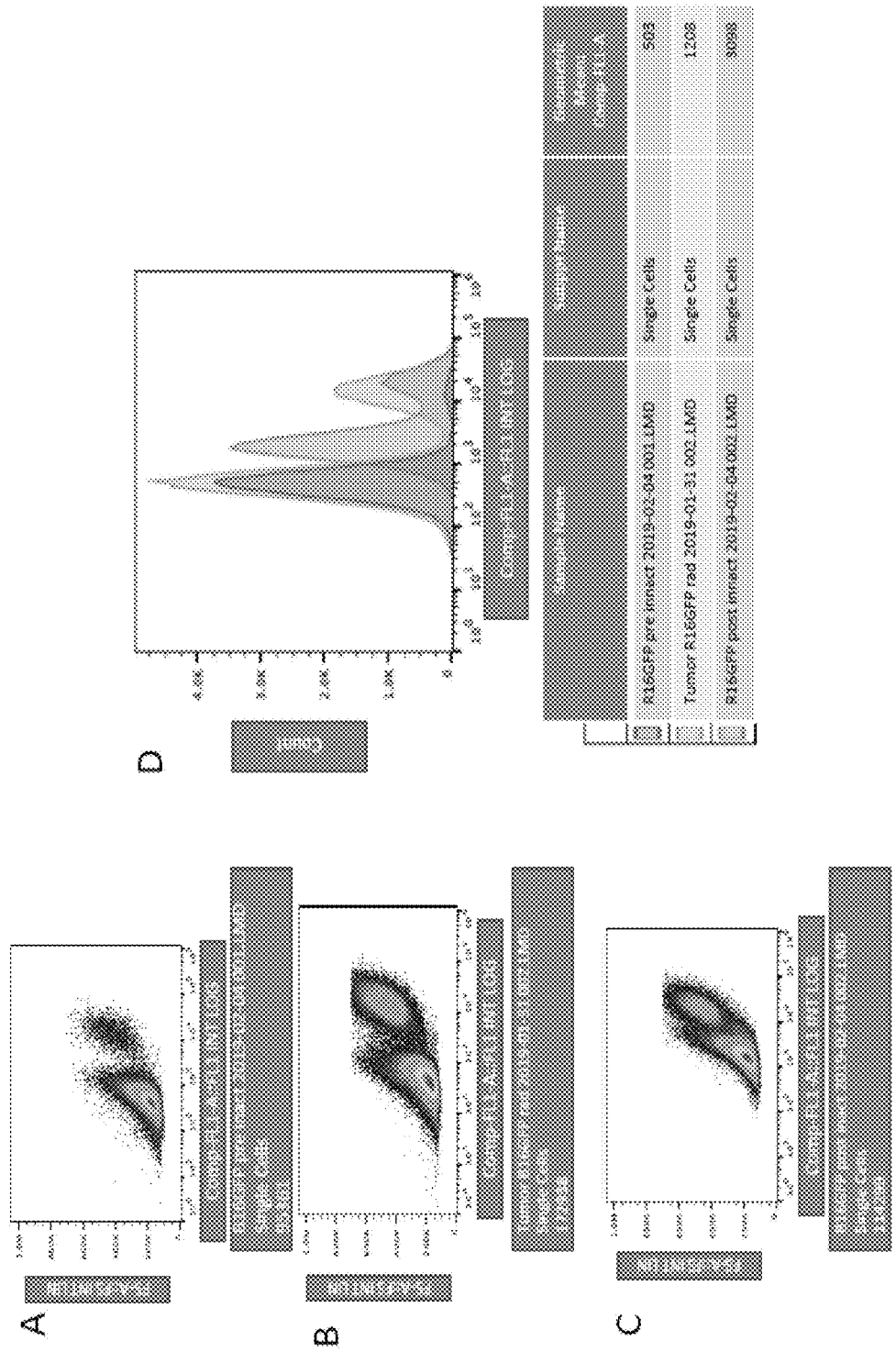
FIG. 23A-D shows GFP expression of mouse melanoma GFP+B16 tumor cells following inactivation by either UV+RF or gamma radiation ex vivo.

The mouse melanoma tumor cell line B16 was transfected with green-fluorescent protein, injected into C571316 mice, removed from the mice, made into a single cell suspension and then was analyzed pre and post UV+RF inactivation and post gamma irradiation (100 Gy) for expression of GFP+ tumor cells. Neither forms of cell inactivation negatively affected the expression of GFP by the tumor cells in the ex vivo tumor tissue (FIG. 23).

Figures 24A, 24B:
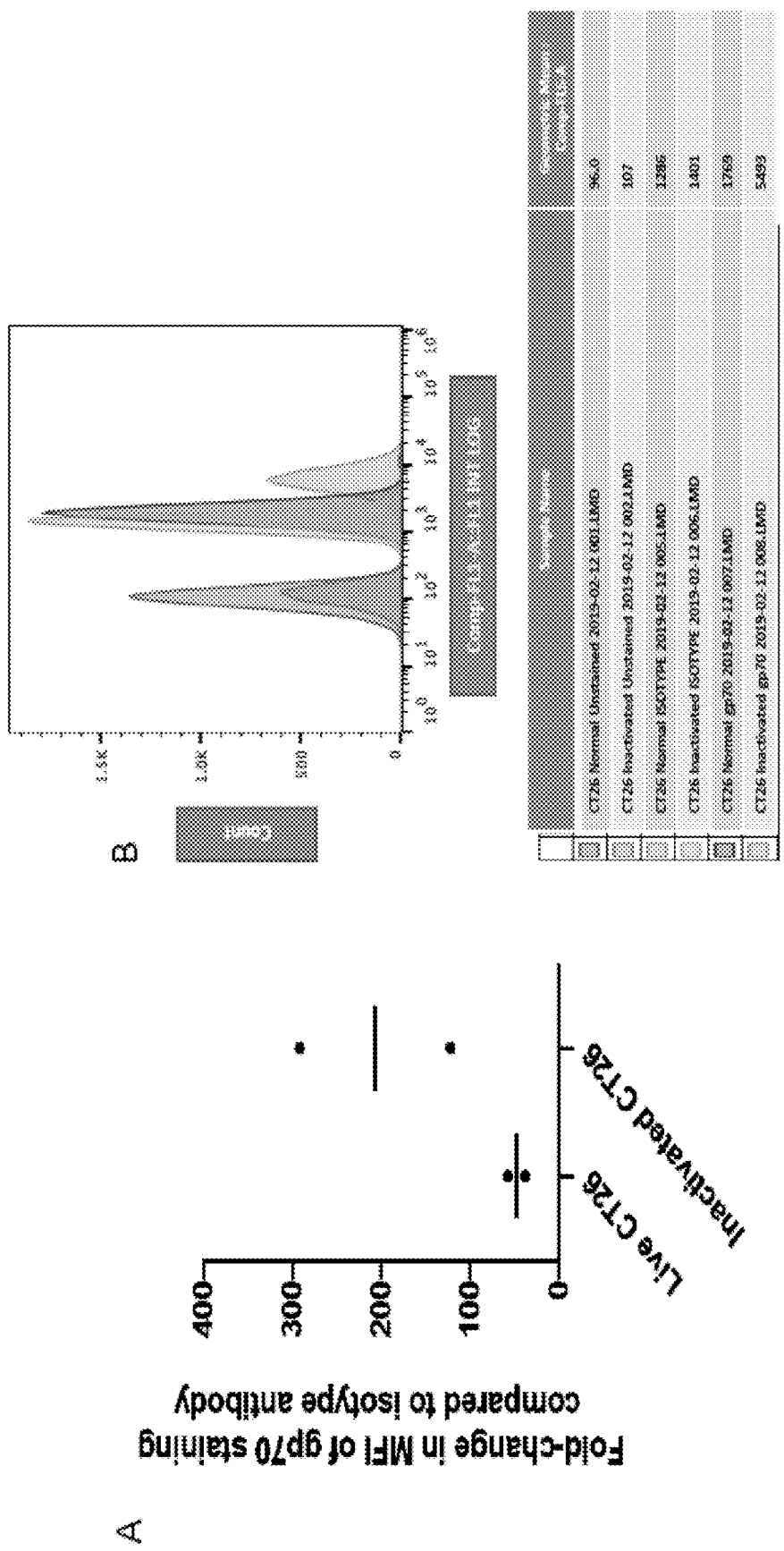
FIG. 24A-B shows expression of the mouse tumor-associated antigen, gp70, following UV+Rf inactivation of mouse colon carcinoma, CT26, tumor cells.
Figures 25A, 25B, 25C, 25D:
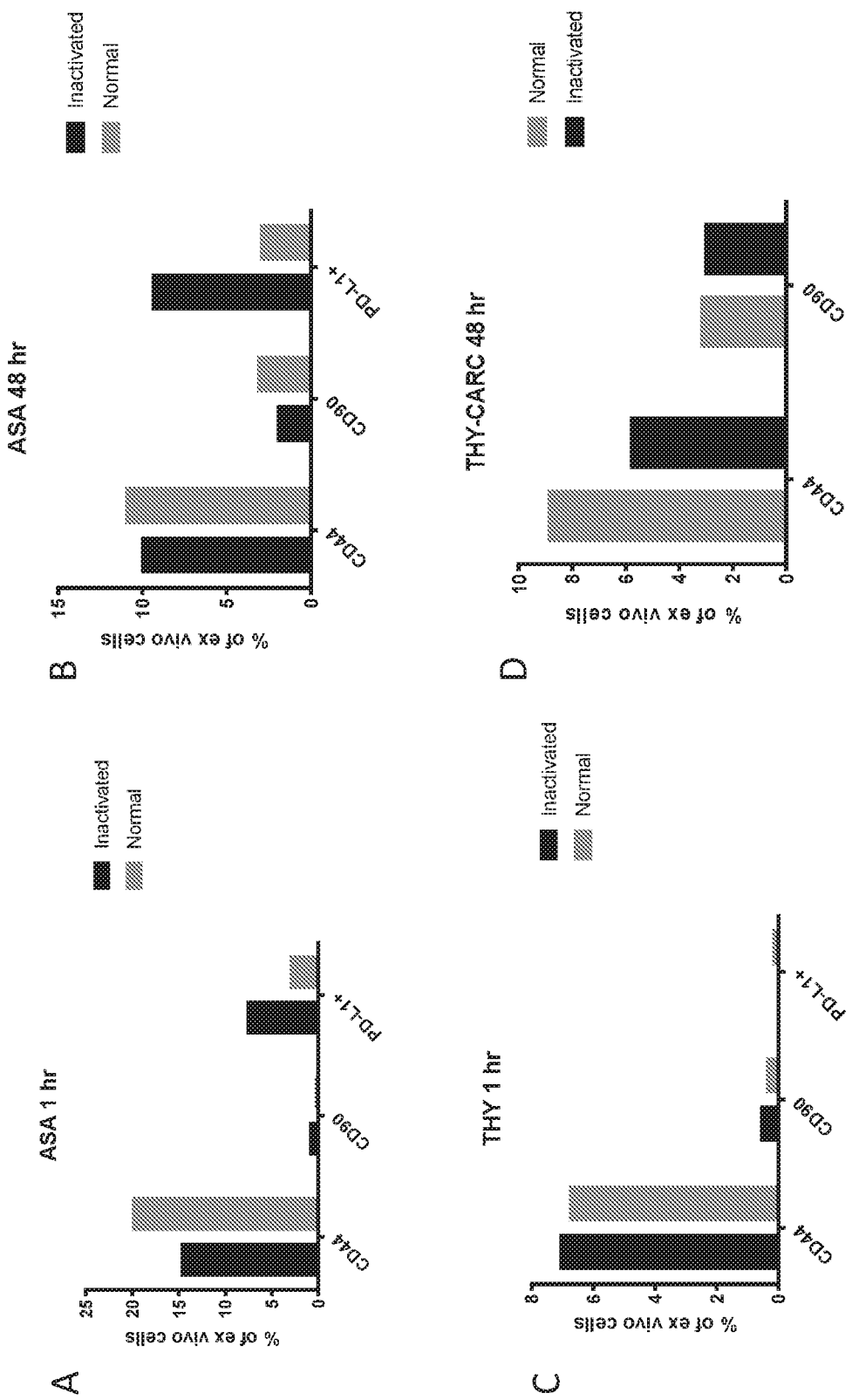
FIG. 25A-D shows surface protein staining of inactivated, ex vivo, canine tumor tissues at 1 hr and 48 hrs after UV+Rf inactivation. Cells were maintained at 4° C. for the 48 hrs after inactivation.

Lastly, the mouse colon carcinoma cell line, CT26, was inactivated with UV+RF and then analyzed for surface expression of the known tumor-associated antigen, gp70 (FIG. 24A-24B). UV+RF inactivation increased the expression of gp70 on the CT26 cells.

Figure 27:
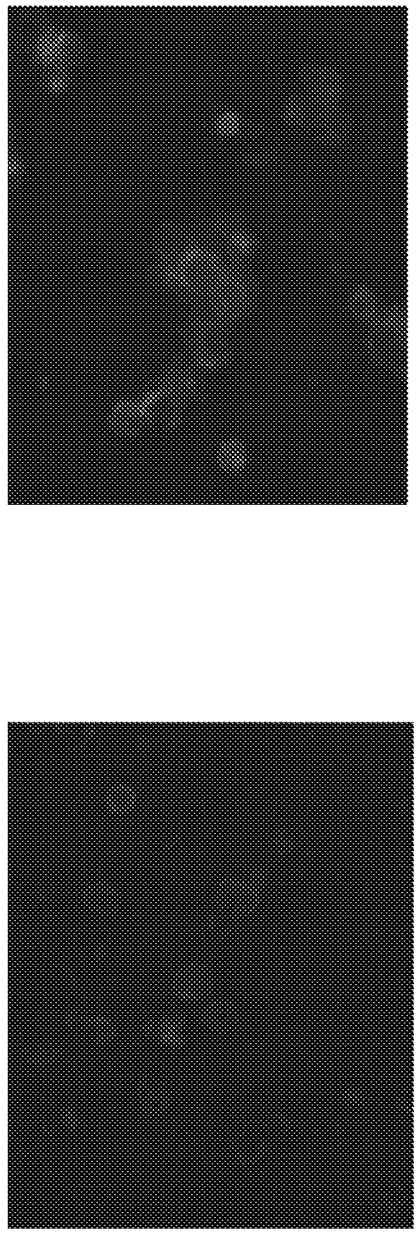
FIG. 27 shows staining of inactivated human liver carcinoma cells, HepG2, for surface marker GLUT1. Inactivated cells are shown in the left panel, and live cells are shown in the right panel. The chart below shows percent antibody-positive and antibody-negative cells when HepG2 cells were stained for surface markers GLUT1 and HLA1.

In addition, the human liver carcinoma cell line, HepG2, was inactivated and stained for expression of human HLA and GLUT1 following UV+RF inactivation (300J, FIG. 27) and imaged on an adherent cell cytometer.

The results obtained from all of these studies indicate that the inactivation can be carried out without significant modification to cell-specific antigens on the cell surface. In addition, these markers are maintained for an extended period of storage post-treatment in morphologicaly intact cells, and these observations have been noted in cells derived from all three species tested (mouse, canine and human).

Example 10. Immune System Triggering by Inactivated Cells

Figures 28A, 28B:
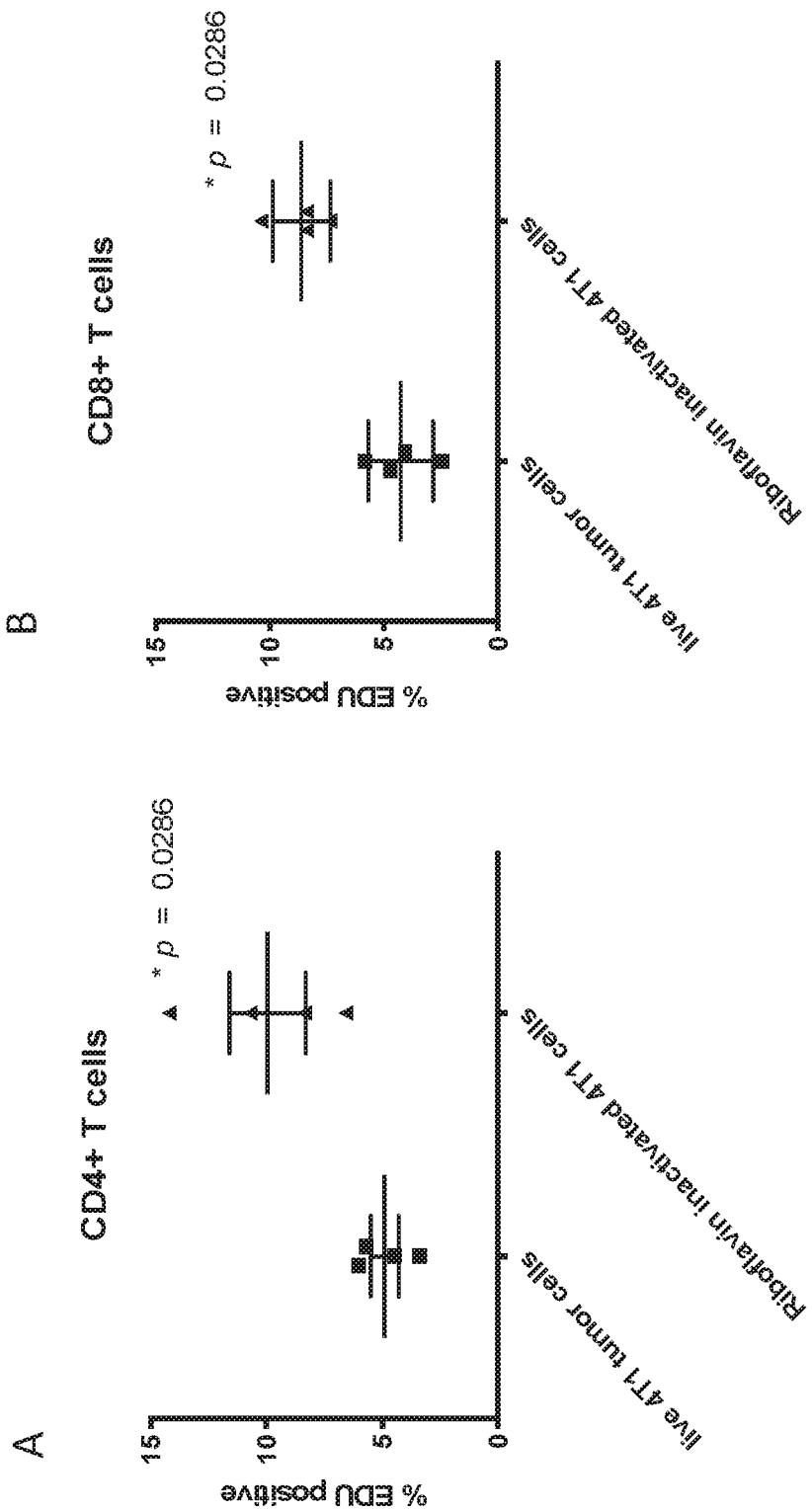
FIG. 28A-B shows proliferation of T cells from spleen of 4T1-tumor bearing mice, that received no treatment. T cells proliferated ex vivo when cultured with inactivated 4T1 tumor cells.

Spleen cells were removed from mice that had 4T1 tumors growing, but did not receive any therapies, and placed them in culture to study T-cell immune response to either live 4T1 cell line derived cells compared to UV+RF-inactivated 4T1 cell line-derived cells (FIG. 28). Spleen cells were plated at $1 \times 10^6$ cells per well, then co-cultured with the tumor cells (live or inactivated) at $4 \times 10^5$ cells per well for 72 hours. The proliferation dye EdU was added after 48 hours of culture. The spleen cells were then collected and stained for proliferation of CD4+ and CD8+ T cells. There was a significant increase in proliferation of both CD4+ and CD8+ T cells when the cells were co-cultured with the UV+RF inactivated 4T1 tumor cells.

Example 11: Pharmacokinetics: Proliferation and Persistence of Tumor Cells In Vitro and In Vivo To test the safety and efficacy of the inactivation process, PyMT tumor cells were removed from solid tumors on B6 mice and inactivated using UV light (300J). $1.5 \times 10^6$ "viable" inactivated PyMT cells were injected s.c. into 5 healthy B6 mice. This was repeated on days 7, 14, and 21 for a total of 4 doses. Mice were euthanized around 160 days after initial inactivated tumor cell injections and dissected. No evidence of tumor growth was noted. To test the safety of the inactivated cells in immune deficient mice, 8 NOD/SCID mice were injected with $1 \times 10^6$ inactivated PyMT cells s.c. in the right flank.

Mice have been monitored since then. Three mice died during the study likely due to unrelated causes (likely a viral or bacterial infection). Necropsy was performed on one and no tumor was noted, skin analysis was performed on the other 2 and no tumors were noted. Mice were euthanized 252 days post tumor cell injection and no tumors were noted in the remaining 5 mice.

Figure 29:
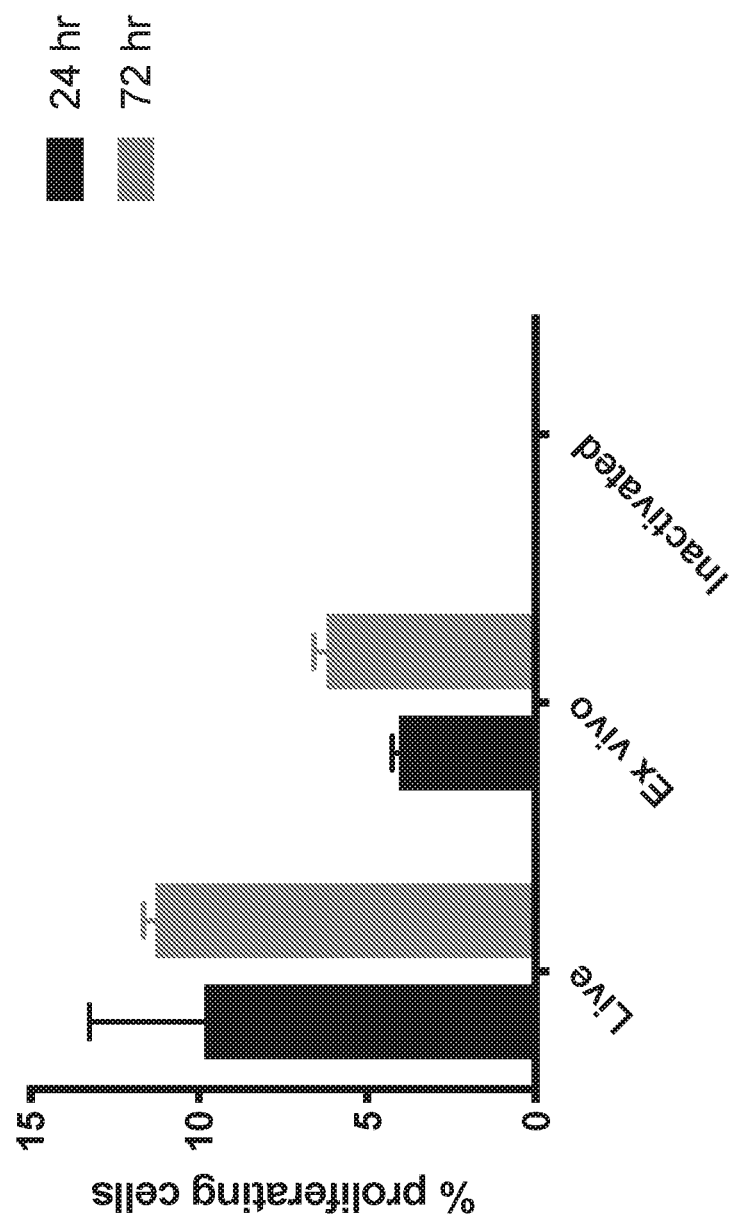
FIG. 29 shows lack of proliferation of inactivated 4T1 mouse breast carcinoma cells in culture for various time points following inactivation.
Figure 30:
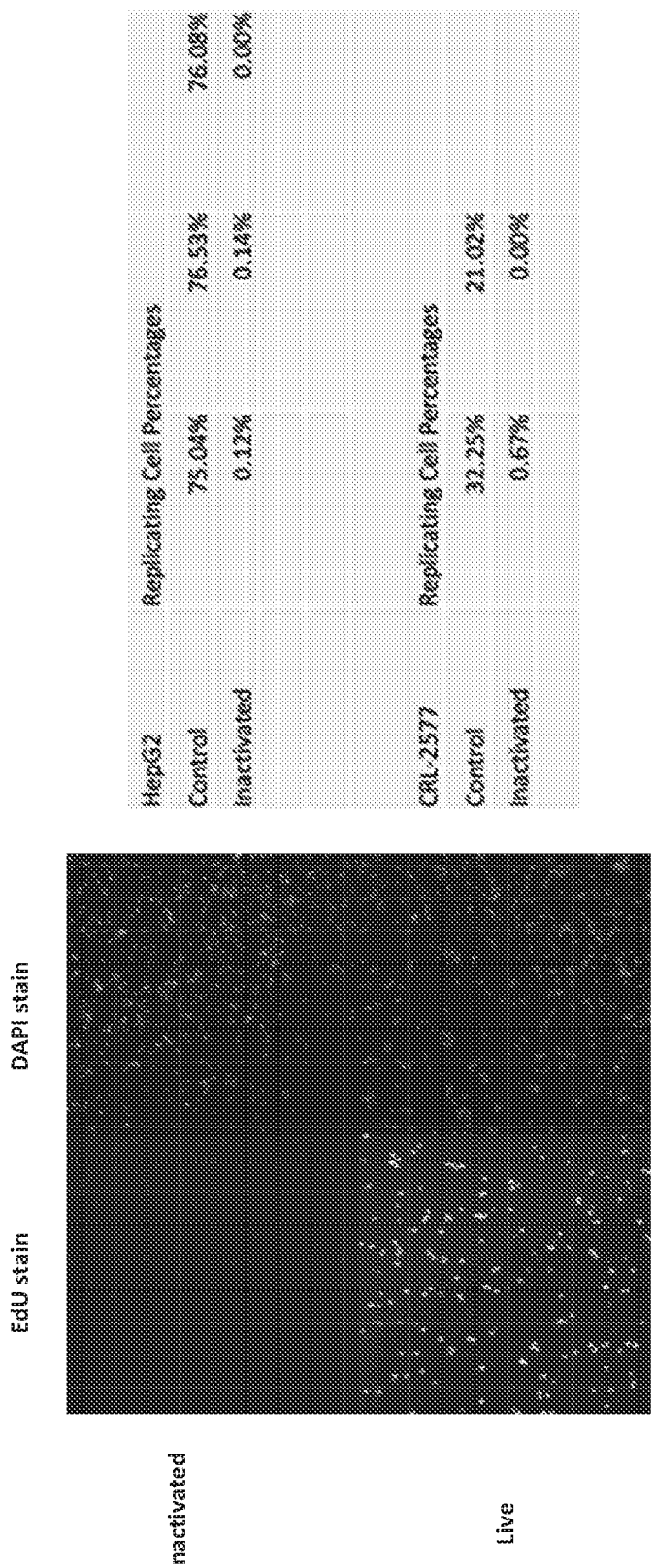
FIG. 30 shows lack of proliferation of inactivated human liver carcinoma cells, HepG2 (left panel) and data for lack of proliferation of HepG2 and human colon carcinoma cells, CRL-2577 (right panel).

Cellular proliferation in culture following inactivation was also assessed (FIG. 29). 4T1 cells were injected into the fat pad of Balb/c mice and tumor growth was monitored until tumors reached about 10 mm in diameter. The tissue was removed, digested using collagenase, washed and inactivated with UV+Rf and then cultured for 24 and 72 hrs in 37° C. No proliferation of 4T1 cells was noted at 24 and 72 hours-post inactivation. This was also compared to the non-inactivated ex vivo tumor cells (which proliferated some) and with the 4T1 tumor cell line (which proliferated). A similar study was performed using the human liver carcinoma cell line, HepG2 and the human colon carcinoma cell line, CRL-2577 (FIG. 30). Proliferation testing was conducted with Click-iT EdU which labels newly formed DNA. Using an adherent cell cytometer the fluorescence of labeled new DNA is compared to a total DNA stain. This test identified many thousands of replicating cells amounting to 20-35% high EdU cells in the live control for CRL-2577 and approximately 75% in the HepG2 population which was labeled for longer.

Although the disclosed teachings have been described with reference to various applications, methods, and compositions, it will be appreciated that various changes and modifications can be made without departing from the teachings herein and the claims below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, GenBank™ or other accession numbers, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A cancer vaccine composition comprising inactivated cancer cells and an adjuvant;
   wherein the cancer cells are inactivated by treating them with UV light comprising a wavelength of 310 nm to 320 nm in the presence of riboflavin;
   wherein the structure of one or more antigenic proteins on the cancer cells is not destroyed by the treatment with UV light;
   wherein the DNA of the inactivated cancer cells comprises oxidized guanine bases;
   wherein the cell membrane integrity and/or the nuclear membrane integrity of the inactivated cancer cells is not compromised; and
   wherein the adjuvant comprises a toll-like receptor 9 (TLR9) agonist.

2. The cancer vaccine composition of claim 1, wherein the expression level of one or more of the following markers on the cancer cells is not significantly increased or decreased before and after treatment with UV light: EpCAM, CD38, CD34, CD117, CD44, CD24, Sca1, HLA, Glut1, MHC Class I, PD-L1, CD45, gp70, GFP and/or CD90.

3. The cancer vaccine composition of claim 1, wherein the cancer cells are breast cancer cells, lung cancer cells, liver cancer cells, bladder cancer cells, gynecological cancer cancers, brain cancer cells, stomach cancer cells, prostate cancer cells, skin cancer cells, thyroid cancer cells, pancreatic cancer cells, colon cancer cells, or blood cancer cells.

4. The cancer vaccine composition of claim 1, wherein the cancer cells are isolated from a subject that has cancer.

5. The cancer vaccine composition of claim 1, wherein the cancer cells are from an immortalized cell line.

6. The cancer vaccine composition of claim 1, wherein the cancer cells are isolated from a tumor mass.

7. The cancer vaccine composition of claim 1, wherein the composition comprises about $1 \times 10^5$ to about $1 \times 10^8$ cancer cells.

8. The cancer vaccine composition of claim 1, wherein the adjuvant comprises CpG oligodeoxynucleotides (ODN).

9. The cancer vaccine composition of claim 1, wherein the composition comprises a pharmaceutically acceptable carrier.

10. The cancer vaccine composition of claim 9, wherein the pharmaceutically acceptable carrier is normal saline, dextrose saline, or phosphate buffered saline.

11. The cancer vaccine composition of claim 1, wherein the treatment with UV light lasts for about 1 minute to about 3 minutes.

12. The cancer vaccine composition of claim 1, wherein the UV light has a wavelength of 310 nm to 315 nm.

13. The cancer vaccine composition of claim 1, wherein the cells are treated with a dose of UV light in the range of about 200 Joules to about 600 Joules.

14. The cancer vaccine composition of claim 13, wherein the dose of UV light is about 300 Joules.

15. The cancer vaccine composition of claim 1, wherein cells are treated with riboflavin at a concentration of about 1 µM to about 50 µM.

16. A method for treating cancer in a subject in need thereof, the method comprising administering the cancer vaccine composition of claim 1 to the subject.

17. The method of claim 16, wherein the cancer is breast cancer, lung cancer, liver cancer, bladder cancer, gynecological cancer, brain cancer, stomach cancer, prostate cancer, skin cancer, thyroid cancer, pancreatic cancer, colon cancer, or blood cancer.

18. A method for producing a cancer vaccine, the method comprising contacting cancer cells with UV light in the presence of riboflavin, wherein the UV light comprises a wavelength of 310 nm to 320 nm.

19. The method of claim 18, wherein the cancer cells are breast cancer cells, lung cancer cells, liver cancer cells, bladder cancer cells, gynecological cancer cancers, brain cancer cells, stomach cancer cells, prostate cancer cells, skin cancer cells, thyroid cancer cells, pancreatic cancer cells, colon cancer cells, or blood cancer cells.

\* \* \* \* \*